(12) United States Patent
Lim

(10) Patent No.: US 9,857,360 B2
(45) Date of Patent: Jan. 2, 2018

(54) CANCER ANALYSIS SYSTEM

(71) Applicant: Xcell Biosciences, Inc., Berkeley, CA (US)

(72) Inventor: James Lim, Oakland, CA (US)

(73) Assignee: XCELL BIOSCIENCES, INC., San Francisco, CA (US)

( * ) Notice: Subject to any disclaimer, the term of this patent is extended or adjusted under 35 U.S.C. 154(b) by 0 days.

(21) Appl. No.: 14/163,456

(22) Filed: Jan. 24, 2014

(65) Prior Publication Data

US 2014/0212895 A1 Jul. 31, 2014

Related U.S. Application Data

(60) Provisional application No. 61/756,993, filed on Jan. 25, 2013, provisional application No. 61/760,626, filed on Feb. 4, 2013.

(51) Int. Cl.
*A61K 38/00* (2006.01)
*G01N 33/50* (2006.01)

(52) U.S. Cl.
CPC ............................. *G01N 33/5091* (2013.01)

(58) Field of Classification Search
None
See application file for complete search history.

(56) References Cited

U.S. PATENT DOCUMENTS

| | | | |
|---|---|---|---|
| 5,330,915 A | 7/1994 | Wilson et al. | |
| 5,922,687 A | 7/1999 | Mann et al. | |
| 6,197,575 B1 | 3/2001 | Griffith et al. | |
| 6,255,495 B1 * | 7/2001 | Yang | C07C 211/22 548/101 |
| 6,322,989 B1 | 11/2001 | Cohen | |
| 6,365,362 B1 | 4/2002 | Terstappen et al. | |
| 6,656,683 B1 | 12/2003 | Reuben et al. | |
| 7,282,350 B2 | 10/2007 | Rao et al. | |
| 7,367,550 B2 | 5/2008 | Lee | |
| 7,476,541 B1 | 1/2009 | Dutra | |
| 7,687,241 B2 | 3/2010 | Chen | |
| 7,785,810 B2 | 8/2010 | Chen | |
| 7,816,138 B2 | 10/2010 | Dutra | |
| 7,819,934 B2 | 10/2010 | Galliher et al. | |
| 7,863,012 B2 | 1/2011 | Rao et al. | |
| 8,039,213 B2 | 10/2011 | Kornblith et al. | |
| 8,071,395 B2 | 12/2011 | Davis et al. | |
| 8,131,053 B2 | 3/2012 | Ortyn et al. | |
| 8,137,912 B2 | 3/2012 | Kapur et al. | |
| 8,288,116 B2 | 10/2012 | Chen | |
| 8,445,225 B2 | 5/2013 | Kuhn et al. | |
| 8,709,793 B2 | 4/2014 | Taboas et al. | |
| 8,906,686 B2 | 12/2014 | Mizuno et al. | |
| 9,029,147 B2 | 5/2015 | Colton et al. | |
| 9,138,460 B2 | 9/2015 | Sevrain et al. | |
| 9,447,378 B2 | 9/2016 | Colton et al. | |
| 2001/0034061 A1 | 10/2001 | Csete et al. | |
| 2003/0092178 A1 | 5/2003 | Yerden et al. | |
| 2004/0152188 A1 | 8/2004 | Yamamoto et al. | |
| 2005/0079557 A1 | 4/2005 | Vendrell et al. | |
| 2005/0101008 A1 | 5/2005 | Diresta et al. | |
| 2005/0181463 A1 | 8/2005 | Rao et al. | |
| 2005/0244843 A1 | 11/2005 | Chen et al. | |
| 2005/0260745 A1 | 11/2005 | Domansky et al. | |
| 2006/0094109 A1 | 5/2006 | Trainer | |
| 2006/0275836 A1 | 12/2006 | Kirkpatrick et al. | |
| 2007/0184033 A1 | 8/2007 | Sevrain et al. | |
| 2007/0298454 A1 | 12/2007 | Green et al. | |
| 2008/0176276 A1 | 7/2008 | Arai | |
| 2008/0305473 A1 | 12/2008 | Chowdary et al. | |
| 2009/0105738 A1 | 4/2009 | Apperson et al. | |
| 2009/0317836 A1 | 12/2009 | Kuhn et al. | |
| 2010/0028915 A1 | 2/2010 | Gualberto et al. | |
| 2010/0104544 A1 | 4/2010 | Atala et al. | |
| 2010/0184219 A1 | 7/2010 | Forsyth | |
| 2010/0216168 A1 | 8/2010 | Heinzman et al. | |
| 2010/0233694 A1 | 9/2010 | Kopf-Sill | |
| 2011/0020930 A1 | 1/2011 | Wise et al. | |
| 2011/0039338 A1 | 2/2011 | Yamanaka et al. | |
| 2011/0053152 A1 | 3/2011 | Goldkorn et al. | |
| 2011/0104718 A1 | 5/2011 | Rao et al. | |

(Continued)

FOREIGN PATENT DOCUMENTS

| | | |
|---|---|---|
| EP | 1697391 B1 | 10/2011 |
| WO | WO-9921533 A2 | 5/1999 |

(Continued)

OTHER PUBLICATIONS

Warburg et al., ( Archives of Biochem , 1958, v.78, pp. 578-586.*
Smith et al Life Science , 2011, p. 1-3.*
Bartlett; et al., "High pressure influences on gene and protein expression. Res. Microbiol. 1995, 146, pp. 697-706."
Koyama; et al., "Post-transcriptional regulation of immunomodulatory cytokines production in human skin fibroblasts by intense mechanical stresses. Journal of Bioscience and Bioengineering. vol. 93, Issue 2, Feb. 2002, pp. 234-239".
Ameri, et al. Circulating tumour cells demonstrate an altered response to hypoxia and an aggressive phenotype. Br J Cancer. Feb. 2, 2010;102(3):561-9. doi: 10.1038/sj.bjc.6605491. Epub Jan. 5, 2010.
Attard, et al. Utilizing circulating tumor cells: challenges and pitfalls. Curr Opin Genet Dev. Feb. 2011;21(1):50-8. doi: 10.1016/j.gde.2010.10.010. Epub Nov. 26, 2010.

(Continued)

*Primary Examiner* — Michail A Belyavskyi
(74) *Attorney, Agent, or Firm* — Wilson Sonsini Goodrich & Rosati

(57) ABSTRACT

The invention provides for detecting target subpopulations of cells that have high proliferative and renewal properties in animals, including circulating tumor cells, cancer stem cells, hematopoietic stem cells and endothelial progenitor cells. The invention utilizes a defined substrate and media of known property to enrich target cell subpopulations which can be used for future genetic, proteomic and morphological analyses. The method can use image-capture and analysis software to characterize cells based on physical properties, such as size, morphology and kinetic properties.

25 Claims, 14 Drawing Sheets

(56) References Cited

U.S. PATENT DOCUMENTS

| | | |
|---|---|---|
| 2011/0129918 A1 | 6/2011 | Hung |
| 2012/0015835 A1 | 1/2012 | Fuchs et al. |
| 2012/0100538 A1 | 4/2012 | Mikolajczyk et al. |
| 2012/0134965 A1 | 5/2012 | Kim et al. |
| 2012/0141547 A1 | 6/2012 | Zhao et al. |
| 2012/0280686 A1 | 11/2012 | White et al. |
| 2013/0164848 A1 | 6/2013 | Munaka et al. |
| 2013/0287743 A1 | 10/2013 | Colton et al. |
| 2015/0023911 A1 | 1/2015 | Schilling et al. |
| 2015/0110749 A1 | 4/2015 | Vacanti et al. |
| 2015/0118755 A1 | 4/2015 | Jaenisch et al. |
| 2015/0247112 A1 | 9/2015 | Orr et al. |
| 2016/0113967 A1 | 4/2016 | Hedrick et al. |
| 2016/0244711 A1 | 8/2016 | Kiyama et al. |

FOREIGN PATENT DOCUMENTS

| | | | |
|---|---|---|---|
| WO | WO 2006108229 | * | 10/2006 |
| WO | WO-2010056328 A1 | | 5/2010 |
| WO | WO 2011/006107 A1 | | 1/2011 |
| WO | WO 2011/113036 A2 | | 9/2011 |
| WO | WO 2012/065067 A2 | | 5/2012 |

OTHER PUBLICATIONS

Bichsel, et al. Diagnostic microchip to assay 3D colony-growth potential of captured circulating tumor cells. Lab Chip. Jul. 7, 2012;12(13):2313-6. doi: 10.1039/c21c40130d. Epub May 8, 2012.

Bondar, et al. Monitoring of the Zeta Potential of Human Cells upon Reduction in Their Viability and Interaction with Polymers. Acta Naturae. 2012; 4:78-81.

Charnley, et al. Integration column: microwell arrays for mammalian cell culture. Integr Biol (Camb). Dec. 2009;1(11-12):625-34. doi: 10.1039/b918172p. Epub Oct. 14, 2009.

Collins. ImageJ for microscopy. Biotechniques. Jul. 2007;43(1 Suppl):25-30.

Cristofanilli, et al. Circulating tumor cells, disease progression, and survival in metastatic breast cancer.N Engl J Med. Aug. 19, 2004;351(8):781-91.

Cristofanilli, et al. Circulating tumor cells: a novel prognostic factor for newly diagnosed metastatic breast cancer. J Clin Oncol. Mar. 1, 2005;23(7):1420-30.

De Giorgi, et al. Circulating tumor cells and [18F]fluorodeoxyglucose positron emission tomography/computed tomography for outcome prediction in metastatic breast cancer. J Clin Oncol. Jul. 10, 2009;27(20):3303-11. doi: 10.1200/JCO.2008. 19.4423. Epub May 18, 2009.

De Mattos-Arruda, et al. Development of molecular biomarkers in individualized treatment of colorectal cancer. Clin Colorectal Cancer. Dec. 2011;10(4):279-89. doi: 10.1016/j.clcc.2011.03.030. Epub May 12, 2011.

Deng, et al. Enrichment with anti-cytokeratin alone or combined with anti-EpCAM antibodies significantly increases the sensitivity for circulating tumor cell detection in metastatic breast cancer patients. Breast Cancer Res. 2008;10(4):R69. doi: 10.1186/bcr2131. Epub Aug. 7, 2008.

Diamandis, et al. Circulating cancer cells and their clinical applications. Clin Chem. Nov. 2011;57(11):1478-84. doi: 10.1373/clinchem.2011.166678. Epub May 17, 2011.

Edelstein, et al. Computer Control of Microscopes Using UNIT 14.20 μManager. Current Protocols in Molecular Biology. 2010; 14.20.1-14.20.17.

Flores, et al. Improving the yield of circulating tumour cells facilitates molecular characterisation and recognition of discordant HER2 amplification in breast cancer. Br J Cancer. May 11, 2010;102(10):1495-502. doi: 10.1038/sj.bjc.6605676.

Generali, et al. Molecular oncology and the neoadjuvant setting: the perfect blend for treatment personalization and clinical trial design. J Natl Cancer Inst Monogr. 2011;2011(43):67-70. doi: 10.1093/jncimonographs/lgr029.

Gorges, et al. Circulating tumour cells escape from EpCAM-based detection due to epithelial-to-mesenchymal transition. BMC Cancer. May 16, 2012;12:178. doi: 10.1186/1471-2407-12-178.

Haltiwanger. The Electrical Properties of Cancer Cells. 2010.

Hayes, et al. Circulating tumor cells at each follow-up time point during therapy of metastatic breast cancer patients predict progression-free and overall survival. Clin Cancer Res. Jul. 15, 2006;12(14 Pt 1):4218-24.

Hope, et al. Acute myeloid leukemia originates from a hierarchy of leukemic stem cell classes that differ in self-renewal capacity. Nat Immunol Jul. 2004;5(7):738-43. Epub. May 30, 2004.

International search report and written opinion dated Jul. 30, 2014 for PCT/US2014/013048.

Issadore, et al. Ultrasensitive clinical enumeration of rare cells ex vivo using a micro-hall detector. Sci Transl Med. Jul. 4, 2012;4(141):141ra92. doi: 10.1126/scitranslmed.3003747.

Jan, et al. Cell adhesion profiling for eukaryotic cell culture. Millipore Corporation. 2007.

Jin, et al. Targeting of CD44 eradicates human acute myeloid leukemic stem cells. Nat Med. Oct. 2006;12(10):1167-74. Epub Sep. 24, 2006.

Jordan, et al. Cancer stem cells. N Engl J Med. Sep. 21, 2006;355(12):1253-61.

Kanof, et al. Preparation of human mononuclear cell populations and subpopulations. Immunologic studies in humans. Current Protocols in Immunology. 1996; Supplement 19.

Kato, et al. Calyculins, potent antitumour metabolites from the marine sponge *Discodermia calyx:* biological activities. Drugs Exp Clin Res. 1988;14(12):723-8.

Kelloff, et al. Cancer biomarkers: selecting the right drug for the right patient. Nat Rev Drug Discov. Feb. 10, 2012;11(3):201-14. doi: 10.1038/nrd3651.

Krebs, et al. Circulating tumor cells: their utility in cancer management and predicting outcomes. Ther Adv Med Oncl. 2010; 2(6):351-365.

Lang, et al. Significance of micrometastasis in bone marrow and blood of operable breast cancer patients: research tool or clinical application? Expert Rev Anticancer Ther. Oct. 2007;7(10):1463-72.

Leary. The Importance of Zeta Potential for Drug/Gene Delivery in Nanomedicine. Malvern Instruments Workshop. Purdue University, West Lafayette, Indiana USA. Sep. 21, 2011.

Lin, et al. Portable filter-based microdevice for detection and characterization of circulating tumor cells. Clin Cancer Res. Oct. 15, 2010;16(20):5011-8. doi: 10.1158/1078-0432.CCR-10-1105. Epub Sep. 28, 2010.

Liu, et al. Rock inhibitor feeder cells induce the conditional reprogramming of epithelial cells. The American Journal of Pathology. 2012; 180(2):599-607.

Lu, et al. Isolation of circulating epithelial and tumor progenitor cells with an invasive phenotype from breast cancer patients. Int. J. Cancer. 2010; 126:669-683.

Lugli, et al. Prognostic impact of the expression of putative cancer stem cell markers CD133, CD166, CD44s, EpCAM, and ALDH1 in colorectal cancer. British Journal of Cancer. 2010; 103:382-390.

Manalo, et al. Transcriptional regulation of vascular endothelial cell responses to hypoxia by HIF-1. Blood. Jan. 15, 2005;105(2):659-69. Epub Sep. 16, 2004.

Mani, et al. The epithelial-mesenchymal transition generates cells with properties of stem cells. Cell. May 16, 2008;133(4):704-15. doi: 10.1016/j.cell.2008.03.027.

McCuskey, et al. The microcirculation during endotoxemia. Cardiovascular Research. 1996; 32:752-763.

Mikolajczyk, et al. Detection of EpCAM-Negative and Cytokeratin-Negative Circulating Tumor Cells in Peripheral Blood. Journal of Oncology. 2011; Article ID 252361, 10 pages. http://dx.doi.org/10.1155/2011/252361.

Nagrath, et al. Isolation of rare circulating tumour cells in cancer patients by microchip technology. Nature. Dec. 20, 2007;450(7173):1235-9.

Ng, et al. Isolation of human and mouse hematopoietic stem cells. Methods Mol Biol. 2009;506:13-21. doi: 10.1007/978-1-59745-409-4_2.

(56) References Cited

OTHER PUBLICATIONS

Oxygen and Cancer: Low Oxygen Levels Breed Cancer . . . Increasing Cellular Oxygen Levels Kills Cancerous Cells. http://www.cancerfightingstrategies.com/oxygen-and-cancer.html#sthash.OrFzrozo.qN7WsJL1.dpbs. 2014.
Ozkumur, et al. Inertial focusing for tumor antigen-dependent and -independent sorting of rare circulating tumor cells. Sci Transl Med. Apr. 3, 2013;5(179):179ra47. doi: 10.1126/scitranslmed.3005616.
Peng, et al. A microfluidic cell culture array with various oxygen tensions. Lab Chip. Aug. 21, 2013;13(16):3239-45. doi: 10.1039/c3lc50388g. Epub Jun. 20, 2013.
Preparation of Human Mononuclear Cell Populations and Subpopulations. (2009). John Wiley & Sons, Inc. Retrieved from http://onlinelibrary.wiley.com/doi/10.1002/0471142735.im07100s85/abstract.
Riethdorf, et al. Disseminated tumor cells in bone marrow and circulating tumor cells in blood of breast cancer patients: current state of detection and characterization. Pathobiology. 2008;75(2):140-8. doi: 10.1159/000123852. Epub Jun. 10, 2008.
Saitoh, et al. Selective inhibition of catalytic activity of smooth muscle myosin light chain kinase. J Biol Chem. Jun. 5, 1987;262(16):7796-801.
Shel Lab. Bactron Anaerobic/Environmental Chambers. Dec. 2013.
Stott, et al. Isolation of circulating tumor cells using a microvortex-generating herringbone-chip. Proc Natl Acad Sci U S A. Oct. 26, 2010;107(43):18392-7. doi: 10.1073/pnas.1012539107. Epub Oct. 7, 2010.
Straight, et al. Dissecting temporal and spatial control of cytokinesis with a myosin II Inhibitor. Science. Mar. 14, 2003;299(5613):1743-7.
Sun, et al. A simple and effective pressure culture system modified from a transwell cell culture system. Biol Res. 2013; 46: 47-52.
Suprynowicz, et al. Conditionally reprogrammed cells represent a stem-like state of adult epithelial cells. Proc Natl Acad Sci. 2012; 109(49):20035-20040.
Wicha, et al. Circulating tumor cells: not all detected cells are bad and not all bad cells are detected. J Clin Oncol. Apr. 20, 2011;29(12):1508-11. doi: 10.1200/JCO.2010.34.0026. Epub Mar. 21, 2011.
Wright, et al. Inexpensive low-oxygen incubators. Nature Protocols. 2006; 4:2088-2090.
Zhang, et al. The identification and characterization of breast cancer CTCs competent for brain metastasis. Sci Transl Med. Apr. 10, 2013 ;5(180):180ra48. doi: 10.1126/scitranslmed.3005109.
Zhang, et al. Zeta potential: a surface electrical characteristic to probe the interaction of nanoparticles with normal and cancer human breast epithelial cells. Biomed Microdevices. 2008; 10:321-328.
Zhe, et al. Circulating tumor cells: finding the needle in the haystack. Am J Cancer Res. 2011;1(6):740-51. Epub Jun. 1, 2011.
Atkuri, et al. Importance of culturing primary lymphocytes at physiological oxygen levels. Proc Natl Acad Sci U S A. Mar. 13, 2007;104(11):4547-52. Epub Mar. 5, 2007.
Bartlett, et al. High pressure influences on gene and protein expression. Res Microbiol. Oct. 1995;146(8):697-706.
Bartlett, et al. Isolation of a gene regulated by hydrostatic pressure in a deep-sea bacterium. Nature. Nov. 30, 1989;342(6249):572-4.
Basson, et al. Effects of increased ambient pressure on colon cancer cell adhesion. J Cell Biochem. Apr. 2000;78(1):47-61.
Boucher, et al. Microvascular pressure is the principal driving force for interstitial hypertension in solid tumors: implications for vascular collapse. Cancer Res. Sep. 15, 1992;52(18):5110-4.
Deguine, et al. Intravital imaging reveals distinct dynamics for natural killer and CD8(+) T cells during tumor regression. Immunity. Oct. 29, 2010;33(4):632-44. doi: 10.1016/j.immuni.2010.09.016. Epub Oct. 14, 2010.
European search report and opinion dated Jul. 25, 2016 for EP Application No. 14743533.3.
Guilak, et al. Control of stem cell fate by physical interactions with the extracellular matrix. Cell Stem Cell. Jul. 2, 2009;5(1):17-26. doi: 10.1016/j.stem.2009.06.016.
Heldin, et al. High interstitial fluid pressure—an obstacle in cancer therapy. Nat Rev Cancer. Oct. 2004;4(10):806-13.
Karagiannis, et al. Cancer-associated fibroblasts drive the progression of metastasis through both paracrine and mechanical pressure on cancer tissue. Mol Cancer Res. Nov. 2012;10(11):1403-18. doi: 10.1158/1541-7786.MCR-12-0307. Epub Sep. 28, 2012.
Li, et al. Hypoxia-inducible factors regulate tumorigenic capacity of glioma stem cells. Cancer Cell. Jun. 2, 2009;15(6):501-13. doi: 10.1016/j.ccr.2009.03.018.
Louie, et al. Identification of a stem-like cell population by exposing metastatic breast cancer cell lines to repetitive cycles of hypoxia and reoxygenation. Breast Cancer Res. 2010;12(6):R94. doi: 10.1186/bcr2773. Epub Nov. 10, 2010.
Mammoto, et al. Mechanical control of tissue and organ development. Development. May 1, 2010; 137(9):1407-1420.
Palazon, et al. Molecular pathways: hypoxia response in immune cells fighting or promoting cancer. Clin Cancer Res. Mar. 1, 2012;18(5):1207-13. doi: 10.1158/1078-0432.CCR-11-1591. Epub Dec. 28, 2011.
Stohrer, et al. Oncotic pressure in solid tumors is elevated. Cancer Res. Aug. 1, 2000;60(15):4251-5.
Su, et al. High extracellular pressure promotes gastric cancer cell adhesion, invasion, migration and suppresses gastric cancer cell differentiation. Oncol Rep. Aug. 2016;36(2):1048-54. doi: 10.3892/or.2016.4841. Epub May 30, 2016.
Suda, et al., Hydrodynamic Gene Delivery: Its Principles and Applications, The American Society of Gene Therapy, Molecular Therapy, Dec. 15, 2007: 2063-2069.
Swartz, et al. Tumor microenvironment complexity: emerging roles in cancer therapy. Cancer Res. May 15, 2012;72(10):2473-80. doi: 10.1158/0008-5472.CAN-12-0122. Epub Mar. 13, 2012.
Tse, et al. Mechanical compression drives cancer cells toward invasive phenotype. Proc Natl Acad Sci U S A. Jan. 17, 2012;109(3):911-6. doi: 10.1073/pnas.1118910109. Epub Dec. 27, 2011.
Wion, et al. PO(2) matters in stem cell culture. Cell Stem Cell. Sep. 4, 2009;5(3):242-3. doi: 10.1016/j.stem.2009.08.009.
Yoshida, et al. Hypoxia enhances the generation of induced pluripotent stem cells. Cell Stem Cell. Sep. 4, 2009;5(3):237-41. doi: 10.1016/j.stem.2009.08.001. Epub Aug. 27, 2009.
Yu, et al. Circulating tumor cells: approaches to isolation and characterization. J Cell Biol. Feb. 7, 2011;192(3):373-82. doi: 10.1083/jcb.201010021.
Mann, et al., Pressure-mediated oligonucleotide transfection of rat and human cardiovascular tissues, Proc. Natl. Acad. Sci. USA, May 1999, 96:6411-16.
Co-pending U.S. Appl. No. 15/629,240, filed Jun. 21, 2017.
Gao, et al. Organoid cultures derived from patients with advanced prostate cancer. Cell. Sep. 25, 2014;159(1):176-87. doi: 10.1016/j.cell.2014.08.016. Epub Sep. 4, 2014.
Kao, et al. Increased hydrostatic pressure enhances motility of lung cancer cells. 2014 36th Annual International Conference of the IEEE, Engineering in Medicine and Biology Society (EMBC). Aug. 26-30, 2014. 2928-2931. DOI: 10.1109/EMBC.2014.6944236.
Lim, et al. Enrichment and characterization of propagating circulating tumor cells from late stage prostate and pancreatic cancer pateitns. Xcell Biosciences. Standford Poster. 2014.
Milosevic, et al. High tumor interstitial fluid pressure identifies cervical cancer patients with improved survival from radiotherapy plus cisplatin versus radiotherapy alone. Int J Cancer. Oct. 1, 2014;135(7):1692-9. doi: 10.1002/ijc.28403. Epub Apr. 25, 2014.
Noman, et al. PD-L1 is a novel direct target of HIF-1α, and its blockade under hypoxia enhanced MDSC-mediated T cell activation. J Exp Med. May 5, 2014;211(5):781-90. doi: 10.1084/jem.20131916. Epub Apr. 28, 2014.
Sottnik, et al. Tumor-induced pressure in the bone microenvironment causes osteocytes to promote the growth of prostate cancer bone metastases. Cancer Res. Jun. 1, 2015;75(11):2151-8. doi: 10.1158/0008-5472.CAN-14-2493. Epub Apr. 8, 2015.

(56) References Cited

OTHER PUBLICATIONS

Tokuda, et al. Effects of Hydrostatic Pressure on Carcinogenic Properties of Epithelia. PLoS One. Dec. 30, 2015;10(12):e0145522. doi: 10.1371/journal.pone.0145522. eCollection 2015.
Williams. Circulating tumor cells. Proc Natl Acad Sci U S A. Mar. 26, 2013;110(13):4861. doi: 10.1073/pnas.1304186110.
Yu, et al. Ex vivo culture of circulating breast tumor cells for individualized testing of drug susceptibility. Science. Jul. 11, 2014; 345 (6193):216-20. doi: 10.1126/science.1253533.
International search report and written opinion dated Sep. 8, 2017 for PCT Application No. US-2017038542.

* cited by examiner

700

705                          710

900

1300

1310

1320

1330

CANCER ANALYSIS SYSTEM

CROSS-REFERENCE

This application claims the benefit of U.S. Provisional Application No. 61/756,993, filed Jan. 25, 2013, and claims the benefit of U.S. Provisional Application No. 61/760,626, filed Feb. 4, 2013, which applications are incorporated herein by reference.

BACKGROUND OF THE INVENTION

Enriched subpopulations of cells from a heterogeneous population of cells are often required for many clinical and research applications. Many subpopulations of cells exist in bodily fluids, including blood. Isolating and examining subpopulations of cells from blood is an attractive option due to the minimally-invasive nature of a venous puncture. Examples of useful cell subpopulations found in the blood can include circulating tumor cells (CTCs), cancer stem cells (CSCs), hematopoietic stem cells (HSCs), and endothelial progenitor cells (EPCs). CTCs and CSCs are of high research and commercial interest due to their critical role during cancer progression, and their potential as a diagnostic and prognostic indicator of patient response to treatment (Cristofanilli et al., *J. Clin. Onc.*, 23(7): 1420-1430, 2005). In addition to their clinical utility, these cancer cells are an important biological source for targeted drug development and discovery of novel biomarkers (De Mattos-Arruda et al., *Clin. Colorectal Can,* 10(4): 279-289, 2011; Generali et al, *J Natl Cancer Inst Monogr* 2011(43): 67-70, 2011; Kelloff and Sigman, *Nature Rev Drug Disc* 11(3): 201-214, 2012; Wicha and Hays *J Clin Onc* 29(12): 1508-1511, 2011). HSCs are rare cells that have the capacity to provide complete restoration of all blood cell lineages after bone marrow ablation and are considered ideal targets for various clinical applications including stem cell transplantation and gene therapy (Ng et al., *Methods Mol Bio,* 506:13-21, 2009). EPCs are a circulating cell population that can be derived from bone marrow and have important regeneration properties.

Recent developments in the life sciences have made it increasingly more important to be able to rapidly and efficiently isolate, characterize, and enrich cell subpopulations from a heterogeneous population without compromising the integrity of the cells. However, a critical problem for the field has been an inability to capture and enrich rare target cell subpopulations in sufficient quantities to conduct meaningful research. The current detection methods for isolating target cell subpopulations often rely on the use of antibodies, ingestion of a matrix, or complex microfluidic devices that have led to inconsistent findings and limited sample (Diamandis et al. *Clin Chem* 57(11): 1478-1484, 2011). Therefore, there exists a need for methods to capture, detect, enrich, and use cell subpopulations for clinical, therapeutic, diagnostic, and research applications.

SUMMARY OF THE INVENTION

Methods, apparatuses, compositions, and kits for detection, isolation, capture, enrichment, and/or characterization of cell subpopulations from a heterogeneous cell population are disclosed, as well as applications thereof.

The invention provides methods for detecting, isolating, and enriching cell subpopulations that have high proliferative and renewal properties from a heterogeneous cell population. The cell subpopulations can be of any type found in a heterogeneous cell population, including rare cell types such as circulating tumor cells (CTC), cancer stem cells (CSC), hematopoietic stem cells (HSC), and endothelial progenitor cells (EPC). The heterogeneous cell population can be a mixture of cells, including a bodily fluid from a subject.

The invention provides a method for detecting, isolating, and/or culturing cells that have high proliferative and renewal properties. The invention utilizes a defined substrate and enrichment media to enrich target cell subpopulations, which have inherent value as a renewable source of cells. Additionally, an image-analysis software is disclosed which can use automated processing to characterize adherent and viable target cell subpopulations enabling high-throughput analysis. Cells are detected by, for example, their size, morphology, and kinetic properties. Furthermore, target cell subpopulations can be cultivated and grown under defined environmental conditions, providing a platform for biomarker testing with a renewable biological source (e.g. dividing CTCs, CSCs, HSCs, and EPCs). The invention also provides a platform for high throughput testing. One non-limiting example is chemosensitivity testing of CTCs and CSCs where both drugs of known utility and those in the experimental phase can be used to screen their respective efficacy in killing cancer cells. Furthermore, the invention can be used to diagnose cancers of unknown origin, determine the efficacy of the cancer treatment regimen for a given patient, and diagnose cancer relapse in patients previously considered in remission.

The cell separation system of the present invention is designed to capture and enrich target cell subpopulations from a heterogeneous population by contacting the target cells to a substrate and incubating the cells in enrichment medium where the target cells are isolated based on their physical characteristics. The target cell subpopulation may be CTCs, CSC, HSCs or EPCs. The heterogeneous cell population may be a bodily fluid that in some instances is mixed with cells that can be marked. In some instances, one or more target cells may be isolated and cultured.

The compositions of the substrate and media can be tailored to the type of target cell subpopulation to be isolated. The media sits adjacent to the substrate and the substrate can be configured in a number of ways.

In some instances, the cell separation system may also employ an apparatus to obtain time-lapse images of the cells and software to perform analysis of the images so that the software may automatically classify cells.

The methods of the invention may be used to obtain target cell types for use in industry or research. The methods of the invention may also be used for the diagnosis, prognosis, and/or theranonsis of a disease, such as cancer. The method of the invention may also be carried out to assess the risk of disease progression.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
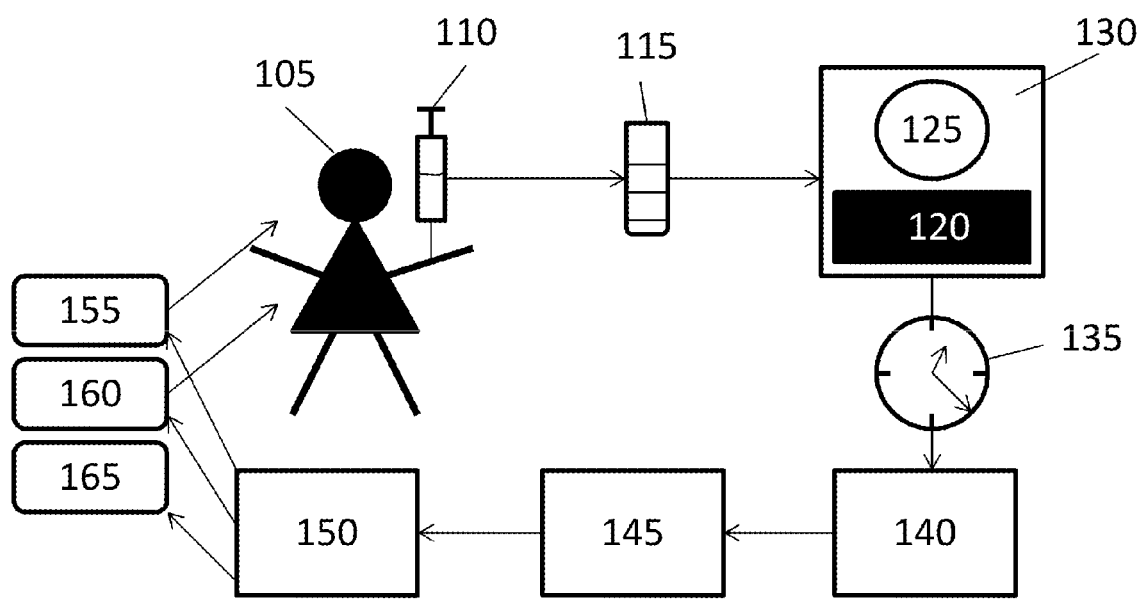
FIG. 1 shows an overall process according to the invention.

While various embodiments of the invention have been shown and described herein, it will be obvious to those skilled in the art that such embodiments are provided by way of example only. Numerous variations, changes, and substitutions may occur by those skilled in the art without departing from the invention. It should be understood that various alternatives to the embodiments of the invention described herein may be employed.

Contents
I. Definitions
II. General Overview
III. Sample Acquisition
  A. Subject
  B. Sample
    i. Optional separation of sample
IV. Substrate
  A. General overview of capturing a target cell subpopulation
  B. Configuration of the substrate
    i. Base layer
    ii. Binding surface layer
    iii. Optional middle layer(s)
    iv. Feeder layer(s)
    v. Conjugating layers
  C. Substrate Compositions
V. Enrichment Media
  A. General overview of enrichment media
  B. Incubation
  C. Enrichment Media Compositions
VI. Software
  A. Identification/classification software
    i. Coordinate system
    ii. Image capture and image stitching
    iii. Identification and classification parameters
    iv. Enhancement of cell detection
  B. System for software facilitation
VII. Microscope and Manipulation Hardware
  A. Microscope
  B. Micromanipulation
VIII. Applications
  A. Source of valuable cells
  B. Personalized Medicine
  C. Treating a patient
IX. Conclusion

I. DEFINITIONS

Certain terms used herein are intended to have the following general definitions:

The term biological specimen generally refers to a sample or part that may show the nature of the whole and examples include, without limitation, bodily fluids, dissociated tumor specimens, cultured cells, and any combination thereof.

Bodily fluid generally refers to fluids or secretions originating from a subject. Bodily fluids can comprise a complex and heterogeneous cell population, and may contain cell types such as CTCs, CSCs, HSCs, and/or EPCs. In some instances, bodily fluids can be a mixture of more than one type of bodily fluid. Some non limiting examples of bodily fluid types are blood, urine, bone marrow, spinal fluid, pleural fluid, lymphatic fluid, amniotic fluid, ascites, sputum, or any combination thereof.

Cancer generally refers to a disease that is characterized by the uncontrolled, abnormal growth of cells. In some instances, cancer can spread.

Cancer stem cells (CSCs) generally refer to a subset of cancer cells that can self-renew. CSCs generally comprise a small proportion of a tumor responsible for its sustained growth and can be responsible for metastasis by giving rise to new tumors. CSCs can express different cell markers than other cells from the same tumor and can contribute to treatment-resistance.

The term cell subpopulation generally refers to a grouping of cells of similar type that can be found in a larger, heterogeneous cell population. Non-limiting examples of cell subpopulations can include: pre-cancerous cells, stem cells, fetal stem cells, undifferentiated stem cells, fetal cells, bone marrow cells, progenitor cells, foam cells, mesenchymal cells, epithelial cells, epithelial progenitor cells, endothelial cells, endothelial progenitor cells (EPCs), endometrial cells, hematopoietic stem cells (HSCs), trophoblasts, cancer cells, circulating tumor cells (CTCs), cancer stem cells (CSCs), red blood cells, white blood cells, immune system cells, and connective tissue cells, or any combination thereof.

Circulating tumor cells (CTCs) generally refer to cancer cells originating from a primary tumor that can circulate in the blood vasculature and/or lymph system.

Culturing cells generally refers to a process by which cells are grown under controlled conditions. The conditions may vary depending on the type of cells to be cultured.

The term cell morphology can be used to refer to the observable physical characteristics of a cell, such as size, shape, or the presence or absence of certain features.

Endothelial progenitor cells (EPCs) generally refers to a population of cells with the ability to differentiate into endothelial cells.

The term enrichment generally refers to increasing the ratio of the number of cells of a target cell subpopulation present to the total number of cells present in a biological mixture of cells. Enrichment can occur, for example, by capturing target cell subpopulations or by proliferation of target cell subpopulations or by a combination thereof.

Hematopoietic stem cells (HSCs) generally refers to multipotent stem cells that can give rise to different blood cell types.

Heterogeneous cell population generally refers to a mixture of two or more cell types. Examples of heterogeneous cell populations can include: bodily fluids, biological specimens, dissociated tumor specimens, cultured cells, and any combination thereof.

Human serum generally refers to a biological fluid originating from humans, whereby the majority of genetic material has been removed and the fluid largely is comprised of, for example, water, enzymes, metabolites, growth factors, signaling peptides, and other proteins native to the host. Some non-limiting examples of sources of human serum include: blood plasma collected form peripheral blood, interstitial fluid, intracellular fluid, and/or transcellular fluid The kinetic properties of a cell generally refer to a cell's ability to move, invade, and/or divide over time.

Micromanipulation, as used herein, generally describes any method for handling single cells. Typical micromanipulation systems can include, for example: an inverted microscope plus a joystick operated, motorized micromanipulation platform; a micropipetter; or laser capture microdissection.

Enrichment media generally refers to a solution in which to bathe and incubate cells that can be used to supply the cells with appropriate nutrients, such that enrichment of a target cell subpopulation can be achieved. In some embodiments, the enrichment media may contain specific upstream ligand-based signaling cues that can potentiate cell division. The exact composition of the enrichment medium can vary based on the cell type to be captured and enriched.

Subject generally refers to a living organism. The methods of the disclosure can be applied to animals including, but not limited to: humans; laboratory animals such as mice, rats, monkeys, and chimpanzees; domestic animals such as dogs and cats, agricultural animals such as cows, horses, pigs, sheep, goats; and wild animals such as bears, pandas, lions, tigers, leopards, elephants, zebras, giraffes, gorillas, dolphins, and whales.

Substrate as used herein, generally refers to the substance that can enhance enrichment, retrieval, capture, and/or proliferation of target cell subpopulations from a heterogeneous cell population. The exact composition of the substrate can be tailored for the enrichment of specific types of target subpopulations of cells. The substrate can be comprised of a single layer or many layers.

The term tumor generally refers to an abnormal mass of tissue resulting from abnormal cell growth and division.

II. GENERAL OVERVIEW

The invention provides methods, apparatuses, compositions, and kits for detecting, isolating, capturing, enriching and characterizing cell subpopulations from a heterogeneous cell population, as well as applications thereof. The cell subpopulations can have high proliferative and renewal properties. The cell subpopulations can be of any type found in a heterogeneous cell population, some non-limiting examples include: circulating tumor cells (CTCs), cancer stem cells (CSCs), hematopoietic stem cells (HSCs), endothelial progenitor cells (EPCs), fetal cells, stem cells, immune cells, epithelial cells, endothelial cells, cancer cells, white blood cells, adult stem cells, and/or epithelial progenitor cells. It will be recognized further that illustrations herein are primarily with reference to isolation of cell subpopulations from blood, but the invention could readily be applied to isolation of cell subpopulations from other heterogeneous cell populations. Such examples include bodily fluids, mixtures of bodily fluids, disassociated tumor samples, cell cultures, or any combination thereof. Furthermore, the bodily fluids, disassociated tumor samples, and cell cultures may be from one or more subjects, or a combination thereof.

FIG. 1 shows an exemplary method according to the disclosure. FIG. 1 shows a process 100 for capturing and enriching target cell subpopulations, in accordance with an embodiment of the invention. The process 100 comprises taking a sample 110 from a subject 105; optionally further separating certain components of the sample 115; plating the cells of the sample on a substrate 120 with enrichment media 125 in an apparatus 130; incubating the samples for a time sufficient for cell division to occur 135. Optionally, the cells may be monitored using a microscope 140 and analysis software 145 which can create an automated or semi-automated output of results 150. The cells and/or results 150 can be used for diagnosis, prognosis, or the monitoring of a disease condition 155, to direct a treatment regimen for a subject 160, and/or for further research 165.

III. SAMPLE ACQUISITION

A. Subject

The subject 105 generally refers to a living organism. In some instances, the subject can be a cancer patient, a patient in remission from cancer, a patient undergoing treatment for cancer, a patient undergoing cancer screening, a patient that is suspected of having cancer, a subject that is cancer-free; a patient who has an autoimmune disease; a patient who is suspected of having an autoimmune disease; a subject donating cells for a bone marrow transplant; a subject receiving bone marrow cells; a cardiovascular disease patient; a patient who has experienced a heart attack or stroke; a patient who is suspected of experiencing a heart attack or stroke; a patient undergoing treatment for wound healing; a patent who may need treatment for wound healing; or any combination thereof.

B. Sample

The sample 110 can be any bodily fluid, biological specimen, a cell culture, a heterogeneous population of cells, or any combination thereof. In some embodiments, the sample is blood taken from a subject by venous puncture; however, the blood can also be obtained through other methods, including arterial puncture or isolation from an umbilical cord. The sample volume may range, for example, approximately between 1 to a 10 mL, approximately between 5 to 20 mL, or approximately between 15 to 35 mL in volume. The sample volume may be approximately 4, 5, 6, 7, 8, 9, 10, 12, 15, 17, 20, 25, 30 or 35 mL in volume but other volumes are contemplated.

The sample may be mixed with one or more samples or cells from the same subject or a different subject. In some instances, a known amount of marked cells may be added to the sample; the marked cells can act as a control to determine the effectiveness of cell capture, the effectiveness of cell proliferation, determine the rate of cell proliferation, or any combination thereof. The cells may be marked by any method known by those skilled in the art, some non-limiting examples include: dyes, fluorescent markers, expression of fluorescent proteins (e.g., green fluorescent protein (GFP), red fluorescent protein (RFP), yellow fluorescent protein (YFP), and etc.), expression of bioluminescent proteins (e.g. luciferase), expression of tagged proteins; use of radioactive molecules, biotin, horseradish peroxidase, fluororescently-conjugated dextran, β-galactosidase, and/or genetic alterations to a cell line or an animal (e.g. cre-lox recombinase system, FLP recombinase, and etc.).

i. Optional Separation of Sample

Figure 2:
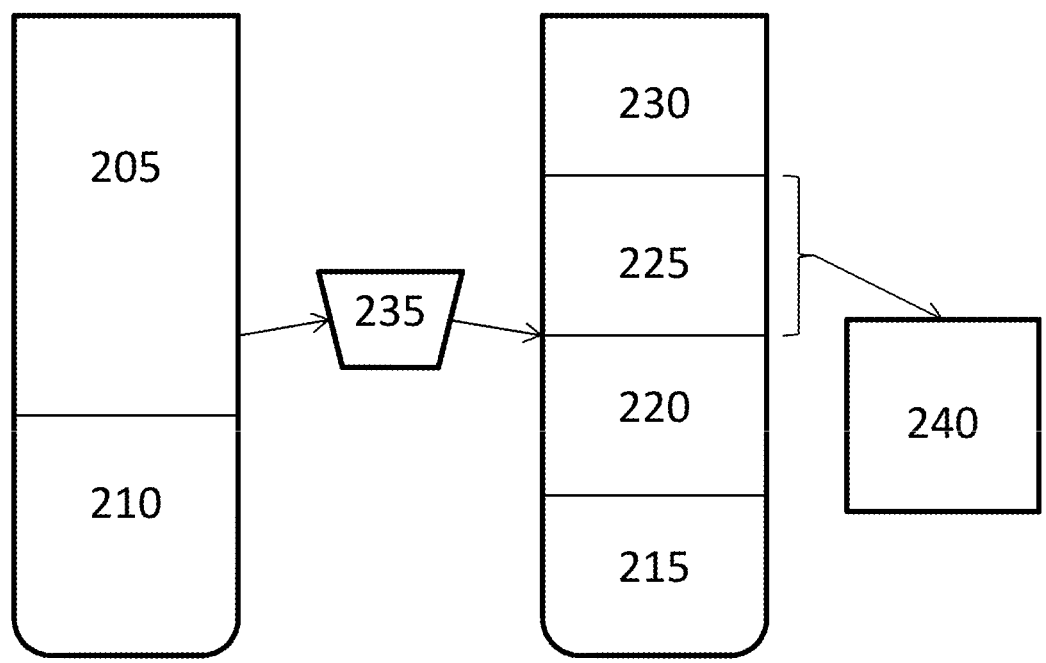
FIG. 2 illustrates an overview of density-based centrifugation of a blood sample using Ficoll reagent to separate the mononuclear cellular layer.

In some instances the cells from the bodily fluid or biological specimen can be separated from other components of the bodily fluid or biological specimen. In the instance where the bodily fluid is blood, the blood components may be separated using a Ficoll reagent, described in detail Fuss et al, *Curr Protoc Immunol* (2009) Chapter 7:Unit 7.1, which is incorporated herein by reference. FIG. 2 shows an exemplary method 200 for separating blood components using a Ficoll reagent (e.g., Ficoll-Paque PLUS, GE Healthcare). The method 200 includes Ficoll reagent 210 and a blood sample 205. When blood combined with Ficoll is subjected to density based centrifugation 235, the components split into four distinct layers: (1) a red blood cell layer 215; (2) a Ficoll layer 220, (3) the mononuclear layer 225, that contains white blood cells and other mononucleated cells (e.g. CTCs, CSCs, HSCs, EPCs, and etc.); and (4) plasma 235. For target cell subpopulation capture, the mononuclear layer can be isolated and exposed to the substrate 240.

IV. SUBSTRATE

A. General Overview of Capturing a Target Cell Subpopulation

Figure 3:
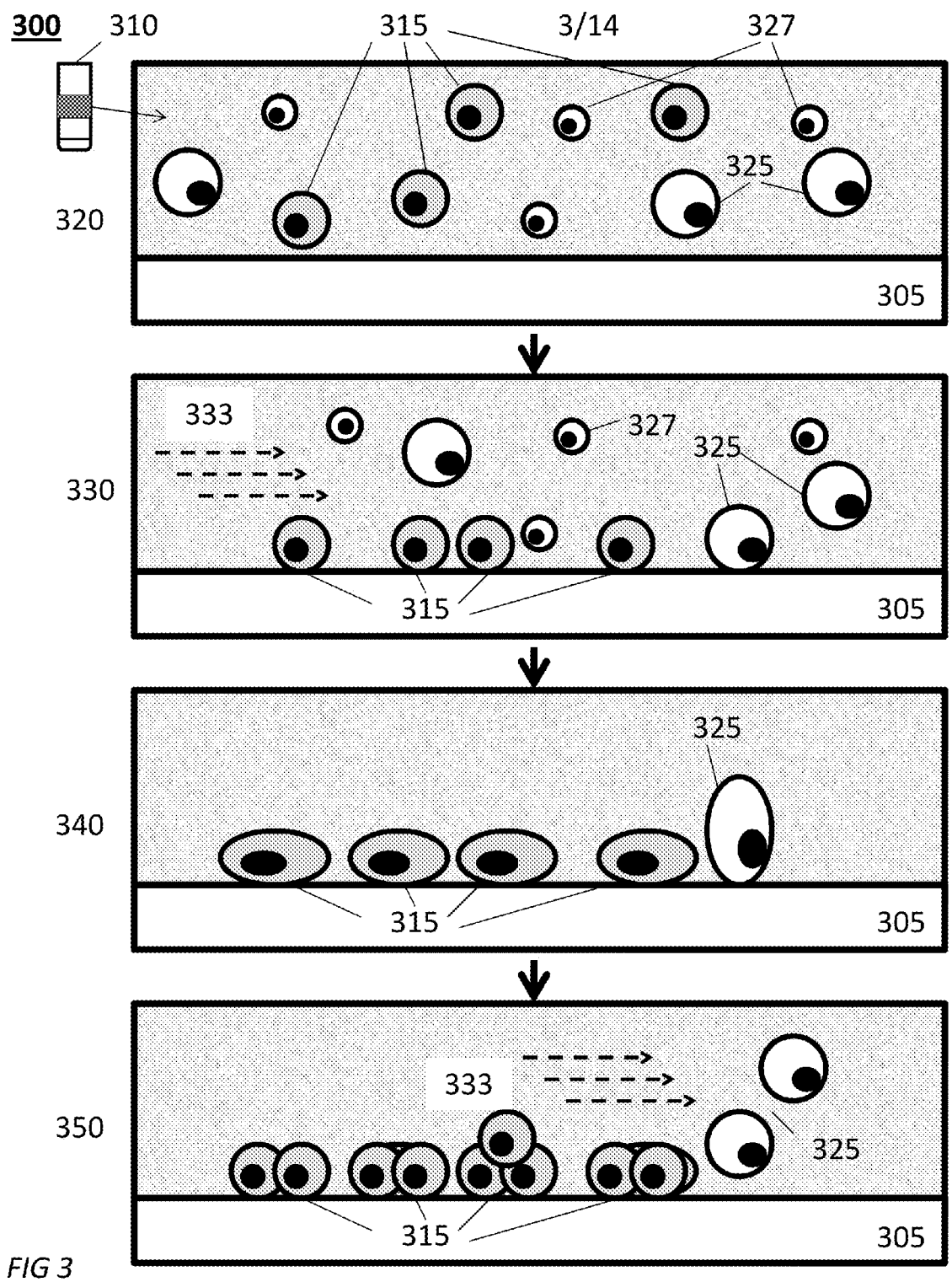
FIG. 3 illustrates a process by which target cell subpopulations can be plated and can adhere to the substrate.

The present invention uses a substrate to capture target cell subpopulations from a sample. FIG. 3 is an illustration diagramming an exemplary method 300 by which a target cell subpopulation 315 can be plated and can adhere to the substrate 305. Panel 320 illustrates a sample 310 that contains a heterogeneous population of cells incubated with a substrate 305. In this illustration, the heterogeneous population of cells contain: a target cell subpopulation 315, white blood cells 325, and other cells 327.

Panel 330 illustrates the target cell subpopulation 315 adhering to the substrate 305 with a higher affinity than white blood cells 325 or other cells 327. Cells that are not adhered to the substrate 305 can be washed away with media 333 or other substance.

Panel 340 shows cells from the target cell subpopulation 315 spreading and beginning a round of cell division on the substrate 305. A captured white blood cell 325 may divide but white blood cells 325 generally do not have the same spreading morphology or kinetic properties as target cell subpopulations 315. Cells that are not in a colony nor adhered to the substrate 305 may be washed away with media 333 or other substance.

Panel 350 depicts captured target cell subpopulations 315 that have undergone one or more rounds of cell division at different rates. Captured white blood cells 325 may proliferate; however white blood cells do not form colonies on the substrate 305.

B. Configuration of the Substrate

Figure 4:
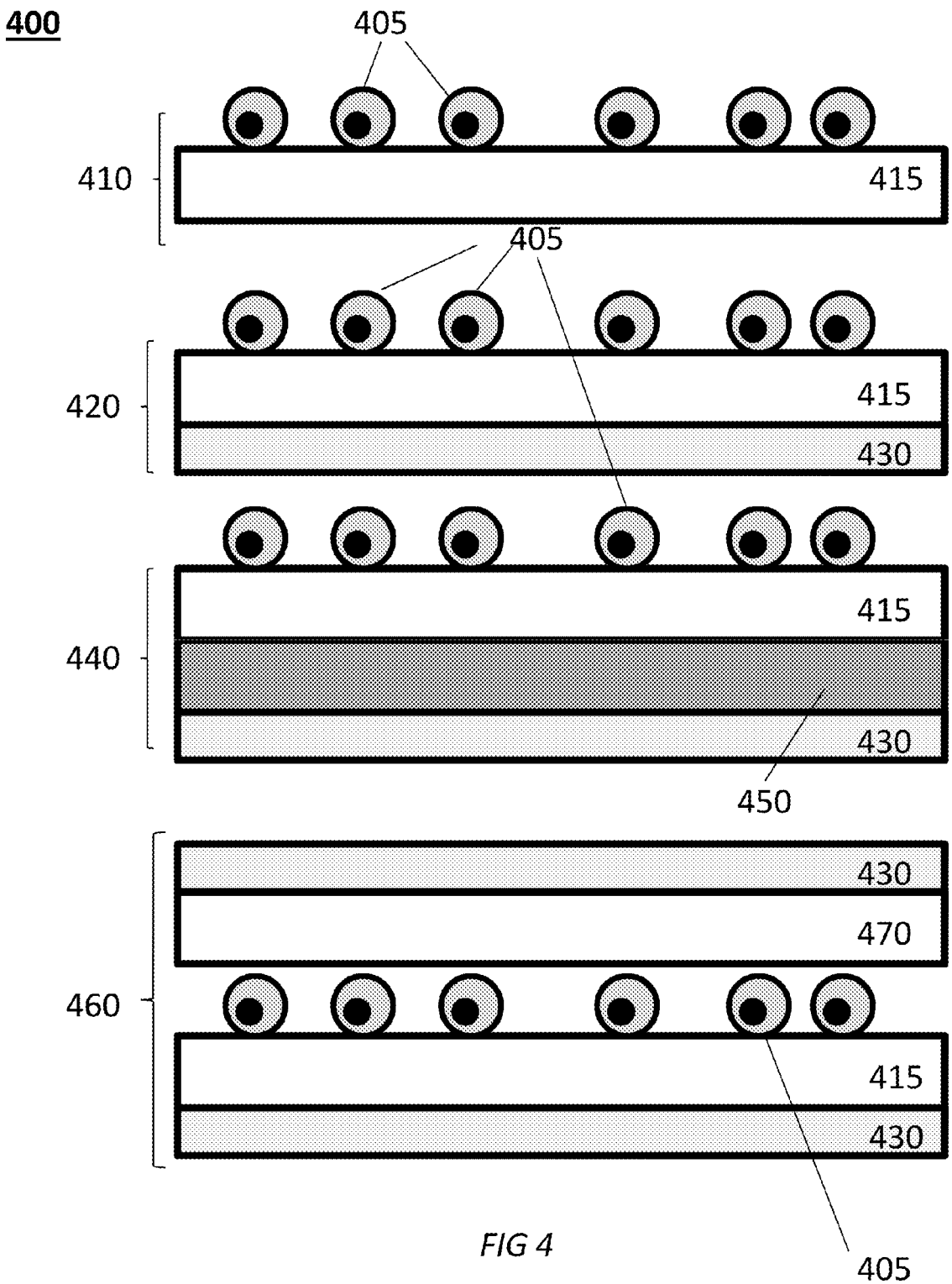
FIG. 4 illustrates different substrate configurations.

The substrate can be comprised of one or more layers. FIG. 4 illustrates several different exemplary configurations of substrates illustrated with captured target cell subpopulations 405. Panel 410 depicts a substrate that has a "single layer" configuration, where the binding surface layer 415 is the only layer. Panel 420 depicts a substrate that has a "two layer" configuration, composed of a base layer 430 adjacent to a binding surface layer 415. Panel 440 depicts a "middle-layer" configuration that is comprised of a base layer 430, one or more middle layer(s) 450, and a binding surface layer 415. Panel 460 illustrates an "inverted" configuration with two base layers 430, a binding surface layer 415, and a feeding layer 470. The inverted configuration creates a semi-sealed chamber wherein the outer layers are facing each other and the distance between the two substrates may range from around 0.1-20 mm, around 1-10 mm, or around 1-5 mm and can be approximately 0.1, 1, 2, 3, 4, 5, 6, 7, 8, 9, 10, 12, 15, 17, or 20 mm.

i. Base Layer

The base layer can be made of plastic, glass, gelatin, polyacrylamide or any combination thereof. In some instances, the material of the base layer may be configured as an apparatus. Examples of such commercially available apparatus' include: microscope slides, culture plates/dishes, Petri dishes, microscope coverslips, an enclosed environmental chamber (e.g. a sealed culture dish), and multi-well culture dishes (e.g., Millicell Cell Culture Inserts; EMD Millipore Corporation).

ii. Binding Surface Layer

The binding surface layer 415 is the portion of the substrate that is in contact with the captured cells. In some instances, the binding surface layer 415 is the only layer, as illustrated in panel 410. In some instances, the binding layer 415 is adjacent to the base layer 430, as illustrated in panels 420 and 460. In other instances, the binding surface layer 415 is separated from the base layer 430 by one or more middle layers 450, as illustrated in panel 440.

The binding surface layer 415 can be comprised of different substances, including cell monolayers, cell lysates, biological materials associated with the extracellular matrix (ECM), gelatin, or any combination thereof.

Such biological materials associated with the ECM can include: collagen type I, collagen type IV, laminin, fibronectin, elastin, reticulin, hygroscopic molecules (glycosaminoglycanse, roteoglycans, glycocalyx), bovine serum albumin, Poly-L-lysine, Poly-D-lysine, and Poly-L-ornithine. There are also commercially available sources of biological materials associated with the ECM, one example of a commercially available source is Matrigel (BD Biosciences). Gelatin can be from an animal source; in some embodiments the gelatin is porcine and/or bovine.

The binding surface layer can be comprised of a monolayer of cells. In some examples, the cells may be, in whole or part, mammalian cells. A mammalian cell line may be, for example, of an endothelial nature and may be of vascular, venous, or capillary origin. Non-limiting examples of mammalian cell lines include human umbilical vein endothelial cells (HUVEC) and human lung microvascular endothelial cells (HLMVEC). The cell lines can be obtained from a primary source or from an immortalized cell line. In some instances, the monolayer of cells may be irradiated by ultraviolet light or X-ray sources to cause senescence of cells (i.e. preventing further cell division). The monolayer may also contain a mixture of one or more different cell types (i.e. cells originating from different lineages or different cell lines). The different cell types may be co-cultured together. One non-limiting example is a combination of primary human endothelial cells co-cultured with transgenic mouse embryonic fibroblasts mixed to form a monolayer.

The binding surface layer may be comprised of a mixture of intracellular components. One method to obtain a mixture of intracellular components is by lysing cells (i.e. disrupting the cellular plasma membrane) and collecting the cytosolic components. The lysed cells may be primary or immortalized. Furthermore, the lysed cells may be from either mono- or co-cultures. Examples of cell lines from which to obtain lysates can include: HUVEC and HLMVEC cells. Cell lysates may be concentrated in their composition by removing excess solution. Excess solution may be removed in several different ways known by those skilled in the art, including: centrifugation, membrane-based dialysis, gas-aided evaporation, or any combination thereof.

The binding surface layer may be comprised of biological materials associated with the extracellular matrix (ECM) or binding moieties. In some instances, gelatin can be mixed directly with cells, binding moieties, biological materials associated with the ECM, or any combination thereof, to make a binding surface layer. In some instances the binding surface layer can be comprised of a commercially available product (e.g. Matrigel (BD Biosciences); Vita-Assay (Vitatex, N.Y.)). In other instances, the binding surface layer can be comprised of a gelatin (e.g. porcine gelatin) mixed with collagens.

iii. Optional Middle Layer(s)

The substrate can have one or more middle layers when the substrate is in the "middle-layer" configuration 440. In a "middle-layer" configuration 440, there may be one or more middle layer(s) 450 between the base layer 430 and the binding surface layer 415. The middle layer(s) of the sandwich may be one or more monolayers of cells. The cells of the monolayer may be of varying origin. One non-limiting example of a middle layer is made by growing a confluent monolayer of mouse embryonic fibroblasts on the base layer and then growing another layer of cells, the binding surface layer, on top of the confluent mouse embryonic fibroblasts.

iv. Feeder Layer(s)

A feeder layer is part of the substrate in the "inverted" configuration 460. A feeder layer 470 sits adjacent to a base layer and is separated from the binding surface layer. Target cell subpopulations 405 preferentially bind to the binding surface layer 475, not the feeder layer 470 as set forth in panel 460. The feeder layer may be a monolayer of feeder cells. The cells of the monolayer may be of varying origin. One non-limiting example of a feeder layer is made by growing a monolayer of human endothelial cells or mouse embryonic fibroblasts on a base layer.

v. Conjugating Layers

Conjugation of layers may be accomplished by allowing cells to grown in a monolayer atop the base layer or middle layer. Conjugation of layers may also be accomplished by pre-treating the surface with a surface of either net positive, net negative, or net neutral charge. The conjugation procedure may be aided by chemical moieties, linkers, protein fragments, nucleotide fragments, or any combination thereof.

C. Substrate Compositions

As one skilled in the art will recognize, the exact configuration and composition of the substrate can be tailored for enrichment of a particular target cell subpopulation. The composition of the substrate may vary based on patient type, cancer type, stage of cancer, patient medical history, and genomic and proteomic analysis of the patient tumor(s).

Figure 7:
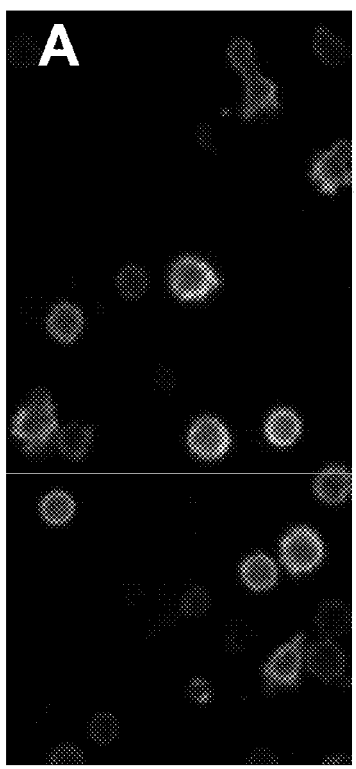
FIG. 7 depicts live-cell imaging of blood spiked with cancer cells that have been plated onto the substrate.
Figure 7:
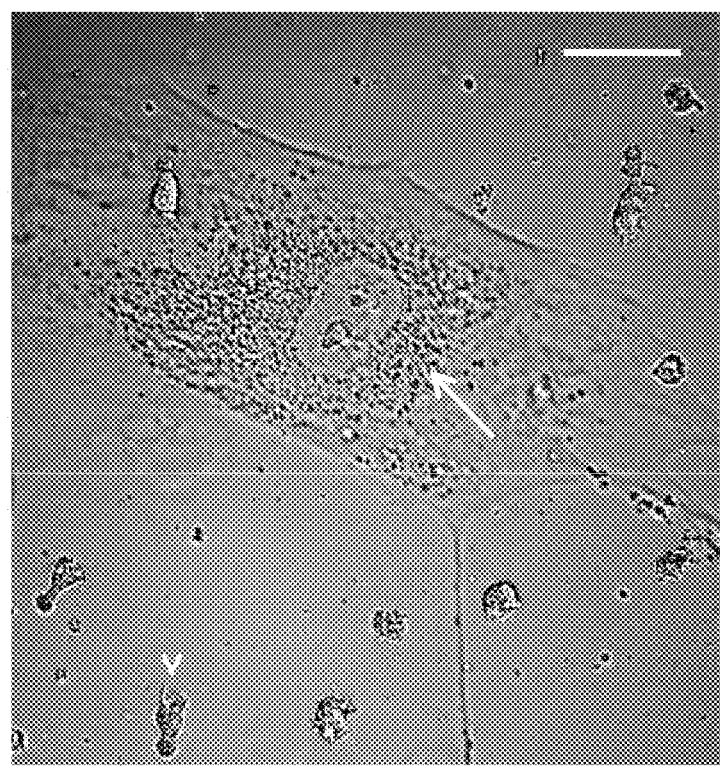

One example of a substrate composition was used in FIG. 7 to test the binding affinity to breast cancer cells. A base layer of 0.1% porcine gelatin was pretreated with 0.1 mg/ml of Poly-L-ornithine (e.g. Poly-L-ornithine hydrochloride or Poly-L-ornithine hydrobromide). After pretreatment, the base layer was treated with approximately 0.1 mg/ml to approximately 1.0 mg/ml of collagen type I, collagen type IV, and laminin. Following preparation of the substrate, blood spiked with MDA-MB231 breast cancer cells was used to test cell binding affinity to the substrate 700 (figure adopted from a color image). Fluorescently conjugated antibodies were used to detect white blood cells 705. Panel 710 depicts a breast cancer cell (arrow) spread on the substrate; white blood cells (small arrowhead) can be distinguished by the software, as described herein.

A second example of a substrate preparation protocol is based on using protein-based substrates. Six or 12-well plates were treated with GOL Substrate or GEL Substrate, ensuring that the substrate covered the entire surface of the well for a minimum of approximately four hours at 37 degrees Celsius. The substrate solution was removed and washed two times with sterile distilled water and 1× phosphate buffered saline (PBS) was added to each well. The 6- or 12-well culture plate was UV-sterilized for a minimum of approximately 4 hours at room temperature.

GOL Substrate is comprised of approximately 0.1% porcine gelatin, approximately 0.05 mg/mL Poly-L-ornithine hydrochloride, and approximately 5% fetal bovine serum (FBS).

GEL Substrate is comprised of approximately 0.1% porcine gelatin, and one or more of the following proteins: approximately 0.1 mg/mL of collagen (e.g. Sigma C7774); approximately 0.1 mg/mL laminin (e.g. Sigma L2020); and/or approximately 0.1 mg/mL fibronectin (e.g. Sigma F0895).

A third example of a substrate preparation protocol is based on using cell-based substrates. Upon introduction of isolated peripheral blood mononuclear cells (PBMC) to the MEF-based substrate; the MEF-culture medium was saved, and replaced with plating culture medium. In one instance, the MEFs were cultured on plates treated with GOL substrate and until cells were at 70% or more confluency (i.e. approximately 48 hours). In another instance, the MEFs were cultured on Millicell insert (Millipore) and a tissue culture plate treated with GOL substrate until cells were at 70% or more confluency (i.e. approximately 48 hours).

V. ENRICHMENT MEDIA

A. General Overview of Enrichment Media

Figure 5:
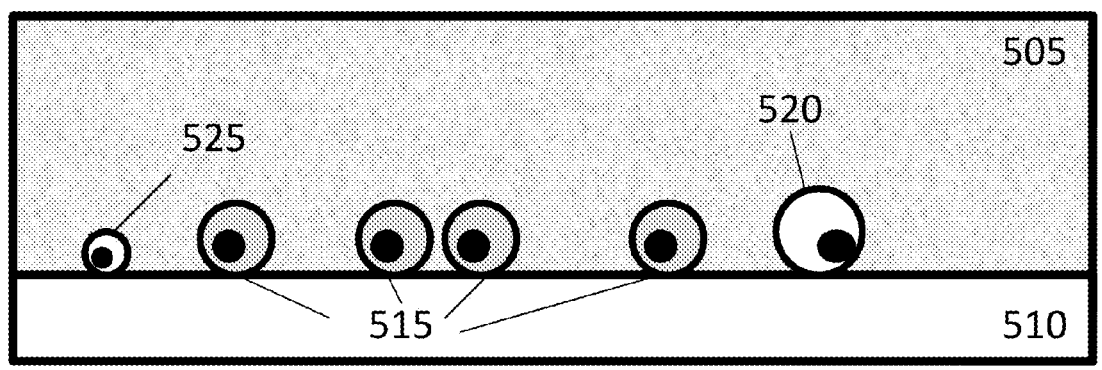
FIG. 5 illustrates enrichment media adapted to promote the proliferation of a target cell subpopulation.
Figure 5:
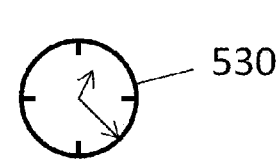
Figure 5:
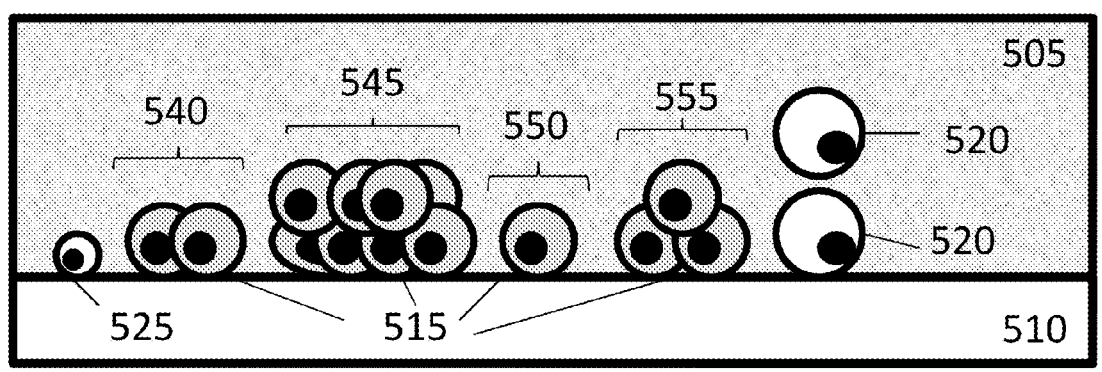

The present invention uses one or more media to specifically enrich target cell subpopulations. FIG. 5 shows an illustration 500 of enrichment media 505 adapted to promote proliferation of the target cell subpopulation, in this illustration the target cell subpopulation are CTCs 515. The composition of the enrichment medium 505 is tailored to the type of cell to be targeted for enrichment. There may be one or more formulations of enrichment media 505 used to enrich cells and the enrichment medium may be changed during the course of cell enrichment. The enrichment media 505 sits adjacent to the substrate 510. In one non-limiting example, the enrichment medium formulation is tailored to cancer type, stage of cancer, patient medical history, and genomic and proteomic analysis of the patient tumor(s). Different types of cells (e.g. non cancerous cells 525, CTCs 515, and white blood cells 520) may be plated on the substrate 510. When the cells are incubated in enrichment media 505 for a period of time sufficient for proliferation 530, the cells can undergo proliferation at different rates. In one example, non cancer cells 525 may not undergo proliferation; CTCs 515 may form subcolonies that undergo proliferation at different rates (e.g., compare: 540, 545, 550, and 555); and white blood cells may undergo proliferation but do not form colonies 520. CTCs 515 may be classified based on their rate of proliferation. One example of a CTC 515 classification scheme is depicted as: non-dividing 550, slow-dividing 540, intermediate-dividing 555, and fast-dividing 545. Classification of cells based on their proliferation capacity in media can be related to the metastatic properties of the CTCs. In some embodiments, the enrichment media, substrate, and pressure conditions work synergistically to improve enrichment of target cells.

The enrichment media 505 can be composed of a primary nutrient source with specific additives to promote cell adherence to the substrate and to ensure long-term cell viability. The primary nutrient source can be derived from mammalian sources, or a mixture of mammalian sources. Some mammalian nutrient sources include but are not limited to: serum derived from calves, horses, goat, mice, rats, and/or humans. In some embodiments, one or more animal serums are mixed. Fetal calf serum and human serum can be mixed together with a mixture ratio of human serum to fetal calf serum of: approximately 1 to 1; approximately 1.5 to 1; or approximately 2 to 1. Additives that may be added include: ions, elements, calcium, glutamate, magnesium, zinc, iron, potassium, sodium, essential amino acids, vitamins, or any combination thereof. In some instances, media culture may be supplemented or made with culture media that has been collected from cell cultures, blood plasma, or any combination thereof. In some instances, more than one type of enrichment media may be used.

B. Incubation

Cells may be incubated in an enclosed environmental chamber (e.g. a sealed culture dish, at defined temperature and gas concentrations. Cells can be cultured at between approximately 34 to approximately 42 degrees Celsius, including approximately 34, 35, 36, 37, 38, 39, 40, 41, or 42 degrees Celsius. Cells can be grown with $CO_2$ levels between approximately 1% to approximately 15% $CO_2$, including approximately 1%, 2%, 3%, 4%, 5%, 6%, 7%, 8%, 9%, 10%, 11%, 12%, 13%, 14% or 15%. Cells can be grown under a variety of hypoxic conditions, with the $O_2$ level ranging from a negligible amount of $O_2$ up to approximately 10% $O_2$, including approximately 0%, 0.1%, 0.5%, 1%, 2%, 3%, 4%, 5%, 6%, 7%, 8%, 9% or 10%. The enclosed environmental chamber can be pressurized. The pressure of the environmental chamber can be set to produce a force equal or greater than the average pressure present in capillaries of the human vasculature system. Pressures can be set between 0.1 to 10 pounds per square inch (PSI). The incubation conditions may vary depending on the type of cell to be proliferated.

C. Enrichment Media Compositions

In one instance, the media is comprised of: RPMI-1640 (e.g., Sigma-Aldrich; R1145), approximately 20% fetal bovine serum; approximately between 0.2 to 1.0 g/L L-glutamine, approximately between 2 to 5 g/L high glucose; approximately 2 g/L sodium bicarbonate; and 25 approximately mM HEPES (e.g., Invitrogen; 15630106).

Plating Culture Medium may be comprised of: F12 medium (e.g., Sigma-Aldrich; N6658), approximately 5 g/L or between approximately 1 to 10 g/L D-(+)-Glucose (e.g., Sigma-Aldrich; G7021); 1× or optionally between 0.1 to 2× Minimum Essential Medium (MEM); approximately 10 mM or between 10 to 25 mM L-glutamine (e.g., Sigma-Aldrich; G7513); approximately 10 mM or between 10 to 25 mM HEPES (e.g., Invitrogen; 15630106); and approximately 20% mammalian serum (e.g. fetal bovine serum, fetal calf serum, horse serum, human serum, human plasma, and etc.).

Type R Long Term Growth Medium may be comprised of: RPMI-1640 based medium (e.g, Sigma-Aldrich; R4130); approximately 5 g/L or approximately 1 to 10 g/L D-(+)-Glucose (e.g., Sigma-Aldrich; G7021); approximately 1×MEM non-essential amino acids (e.g., Sigma-Aldrich; M7145); approximately 1×RPMI vitamins (e.g., Sigma-Aldrich; R7256); approximately 10 mM or between approximately 1 to 20 mM L-glutamine (e.g., Sigma-Aldrich; G7513); approximately 20% or between 5% to 50% mammalian serum (e.g. fetal bovine serum, fetal calf serum, horse serum, human serum, human plasma, and etc.). Optimally, the pH of the Type R Long Term Growth Medium can be adjusted to approximately 7.2 but the pH can range from approximately 6 to 8. Optional Type R Long Term Growth Medium supplements can include: 5 μg/mL or approximately 1 to 10 μg/mL insulin (e.g. recombinant human insulin (rh insulin)); 50 μg/mL or approximately 10 to 100 μg/mL ascorbic acid; 5 ng/mL or approximately 1 to 20 ng/mL epidermal growth factor (EGF) (e.g. recombinant human (rhEGF)); 0.75 units/mL heparin sulfate; 1 μg/mL or approximately 0.5 to 2 μg/mL hydrocortisone hemisuccinate; 15 ng/mL or approximately 5 to 30 ng/mL insulin-like growth factor 1 (IGF-1) (e.g. rhIGF-1); 1 unit/mL or approximately 1 to 10 units/mL penicillin; 1 μg/mL or approximately 1 to 10 μg/mL streptomycin; approximately 0.1 to 25 ng/mL Amphotericin B; or any combination thereof.

Type DF Long Term Growth Medium may be comprised of: DMEM/F12 medium (e.g., Sigma-Aldrich; 51445C); 5 g/L or approximately 1 to 10 g/L D-(+)-Glucose (Sigma-Aldrich; G7021); approximately 1× MEM non-essential amino acids (Sigma-Aldrich; M7145); 10 mM or approximately 1 to 20 mM L-glutamine (e.g., Sigma-Aldrich; G7513); and 20% or approximately 5% to 50% mammalian serum (e.g. (e.g. fetal bovine serum, fetal calf serum, horse serum, human serum, human plasma, and etc.). Optimally, the pH of the Type DF Long Term Growth Medium can be adjusted to approximately 7.2 but the pH can range from approximately 6 to 8. Optional Type DF Long Term Growth Medium supplements can include: approximately 10 mM or between 10 to 25 mM HEPES (e.g., Invitrogen; 15630106); 5 μg/mL or approximately 1 to 10 μg/mL insulin (e.g. recombinant human insulin (rh insulin)); 50 μg/mL or approximately 10 to 100 μg/mL ascorbic acid; 5 ng/mL or approximately 1 to 20 ng/mL epidermal growth factor (EGF) (e.g. recombinant human (rhEGF)); 0.75 units/mL heparin sulfate; 1 μg/mL or approximately 0.5 to 2 μg/mL hydrocortisone hemisuccinate; 15 ng/mL or approximately 5 to 30 ng/mL insulin-like growth factor 1 (IGF-1) (e.g. rhIGF-1); 1 unit/mL or approximately 1 to 10 units/mL penicillin; 1 μg/mL or approximately 1 to 10 μg/mL streptomycin; approximately 0.1 to 25 ng/mL Amphotericin B; or any combination thereof.

Type D Long Term Growth Medium may be comprised of: DMEM medium, high glucose (Sigma-Aldrich; D6429); 5 g/L or approximately 1 to 10 g/L D-(+)-Glucose (Sigma-Aldrich; G7021); approximately 1×MEM non-essential amino acids (Sigma-Aldrich; M7145); 10 mM or approximately 1 to 20 mM L-glutamine (e.g., Sigma-Aldrich; G7513); and 20% or approximately 5 to 50% mammalian serum (e.g. fetal bovine serum, fetal calf serum, horse serum, human serum, human plasma, and etc.). Optimally, the pH of the Type D Long Term Growth Medium can be adjusted to approximately 7.2 but the pH can range from approximately 6 to 8. Optional Type D Long Term Growth Medium supplements can include: 10 mM or between 10 to 25 mM HEPES (e.g., Invitrogen; 15630106); 5 µg/mL or approximately 1 to 10 µg/mL insulin (e.g. recombinant human insulin (rh insulin)); 50 µg/mL or approximately 10 to 100 µg/mL ascorbic acid; 5 ng/mL or approximately 1 to 20 ng/mL epidermal growth factor (EGF) (e.g. recombinant human (rhEGF)); 0.75 units/mL heparin sulfate; 1 µg/mL or approximately 0.5 to 2 µg/mL hydrocortisone hemisuccinate; 15 ng/mL or approximately 5 to 30 ng/mL insulin-like growth factor 1 (IGF-1) (e.g. rhIGF-1); 1 unit/mL or approximately 1 to 10 units/mL penicillin; 1 µg/mL or approximately 1 to 10 µg/mL streptomycin; approximately 0.1 to 25 ng/mL Amphotericin B; or any combination thereof.

Mouse Embryonic Fibroblast (MEF)-Enriched Medium can be comprised of: DMEM medium, high glucose (Sigma-Aldrich; D6429); 5 g/L or approximately 1 to 10 g/L D-(+)-Glucose (Sigma-Aldrich; G7021); approximately 1×MEM non-essential amino acids (Sigma-Aldrich; M7145); 10 mM or approximately 1 to 20 mM L-glutamine (e.g., Sigma-Aldrich; G7513); 10 mM or between 10 to 25 mM HEPES (e.g., Invitrogen; 15630106); approximately 10% mammalian serum (e.g. fetal bovine serum, fetal calf serum, horse serum, human serum, human plasma, and etc.). MEF medium becomes "enriched" after being cultured in the presence of MEF cells. In some embodiments, the MEF cells are cultured for a minimum of 48 hours, until the cell confluency is at least 70%.

One example of a target cell subpopulation culturing protocol that uses a protein-based substrate is as follows. Peripheral blood mononucleated cells (PBMCs) were purified by Ficoll-based density centrifugation a desired substrate in 6-well or 12-well standard size plates (BD biosciences). Plating Culture Medium was added (e.g. 2 mL/per well in a 6-well plate or 1 mL/well in a 12-well plate). 300 uL of PBMC solution (obtained from 20 mL of peripheral blood, resuspended in 2 mL of Plating Culture Medium) was added to each well for a 6-well plate (150 uL for 12-well plates). The plates were incubated at 37 degrees Celsius at 5% $CO_2$ for 1 hour. One hour after initial plating, the cell culture plates were tapped several times to remove loosely attached cells (e.g. white blood cells), and the media was exchanged with pre-warmed Plating Culture Medium. The plates were then incubated in a pressurized incubator at 2 PSI, 37 degrees Celsius, with 5% $CO_2$, 2% $O_2$, and 93% $N_2$ for a minimum of 24 hours. After a minimum of 24 hours had passed the cell culture plates were tapped several times to remove loosely attached cells and the media was exchanged with pre-warmed Long Term Growth Medium. The cells were incubated in a pressurized incubator at 2 PSI, 37 degrees Celsius, 5% $CO_2$, 2% $O_2$, and 93% $N_2$. Every 72 hours, approximately one third to one half of the Long Term Growth Medium was replaced with pre-warmed fresh media.

Figure 13:
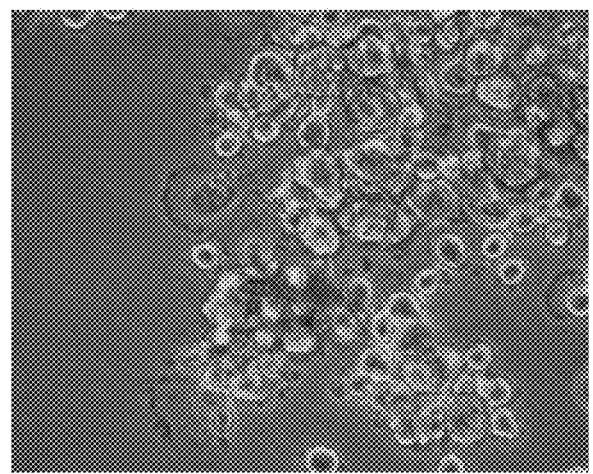
FIG. 13 depicts images of an enriched target cell subpopulation.
Figure 13:
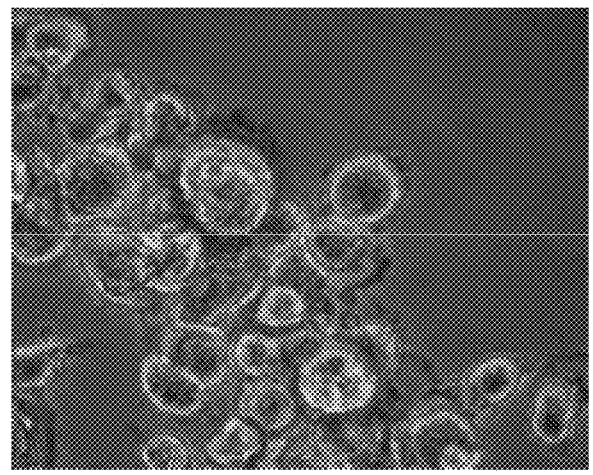
Figure 13:
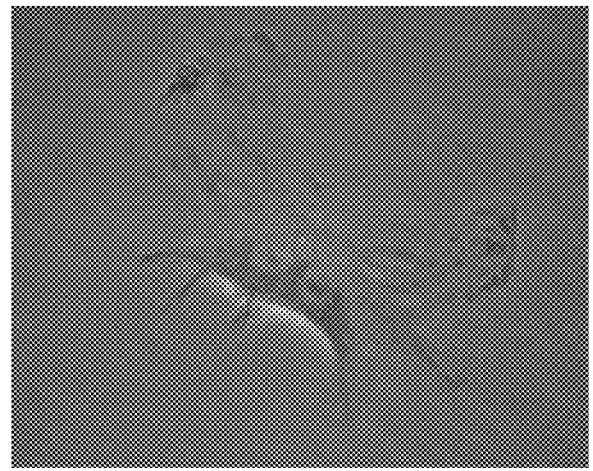

A second example of a target cell subpopulation culturing protocol that uses a cell-based substrate is as follows. FIG. 13 shows cells grown from this protocol. PBMCs spiked with CTC cells from a patient were purified using Ficoll-based density centrifugation onto the GOL substrate. Freshly isolated cells were resuspended into Plating Culture Medium. A 6-well or 12-well standard size culture plate was used. The culture plate was pre-treated for a minimum of 48 hours with irradiated or non-irradated MEF cells, until the MEF cells reached a confluency of at least approximately 70%. The MEF-enriched Culture Medium was exchanged with Plating Culture Medium. The MEF-Enriched Culture Medium was retained. Peripherial blood mononuclear cell (PBMC) Solution was generated using 20 mL of peripheral blood, spun down, and resuspended in 2 mL of Plating Culture Medium. PBMC solution was added to each well of the culture dish and cells were incubated 37 degrees Celcius with 5% $CO_2$ for 1 hour. One hour after initial plating, the culture plate was tapped several times to remove loosely attached cells and the media was exchanged with the previously retained MEF-Enriched Culture Medium. The plates were incubated in a pressurized incubator under the following conditions: 2 PSI, 37 degrees Celsius, 5% $CO_2$, 2% $O_2$, and 93% $N_2$ for a minimum of 48 hours. After 48 hours had passed, approximately one third to one half of the MEF-Enriched Media was exchanged with pre-warmed Type R Long Term Growth Medium. The cells were then incubated again in a pressurized incubator under the following conditions: 2 PSI, 37 degrees Celsius, 5% $CO_2$, 2% $O_2$, and 93% $N_2$ for a minimum of 48 hours. Again, half to one third of the medium was replaced with fresh, pre-warmed Type R Long Term Growth Media. Every 72 hours, approximately one half to one third of the Type R Long Term Growth Medium was replaced with pre-warmed fresh media. CTCs enriched using this protocol are depicted in 1300. Panel 1310 shows CTCs isolated from a patient under 10× magnification; panel 1320 shows the same CTC cells under 20× magnification. Panel 1330 shows a multi-nucleated CTC cell at 20× magnification. The presence of one more nuclei within a single cell can indicate improper cell cycle control, often associated cancers.

VII. SOFTWARE

A. Identification/Classification Software
i. Coordinate System

An aspect of the invention is software configured to implement the method of semi-automated or automated identification and classification of target cell subpopulations based on their physical characteristics. The software can measure the physical characteristics over time in a coordinate system 1200. The software is configured to create a virtual coordinate system 1220 to reference the location of detected target cell subpopulations on a substrate in a culture dish 1210. The virtual coordinate system is propagated by aligning the culture dish to a user-defined point of origin ("point of origin") 1230 and a virtual grid 1220 that is made up of scalable vector quadrants is overlaid 1200. In a most preferred embodiment, the virtual coordinate system is used by the image acquisition system to facilitate an automated time-lapse capture across the entire surface of a culture dish. Some examples of standard-sized culture dishes that have been used include: 10 mm, 35 mm, 60 mm, and 100 mm and standard highthroughput plates (e.g. 6 well, 12 well, 24 well) but other sizes of culture dishes are contemplated. In one embodiment, an operator can revisit the location of specific colonies of particular interest, and cells can be collected through the use of a micromanipulator and transjector (see e.g. FIG. 8). An individual cell may be captured for use in targeted biomedical studies or can be harvested and used for further culturing experiments.

ii. Image Capture and Image Stitching

The software uses the coordinate system 1200 to automatically capture, recombine, realign, and/or optimize images. This automated stitching process creates a single stitched image for a given time point. In some cases, a stitched image can encompass between approximately 25 to approximately 200 images. Stitched images may undergo an initialization process whereby the images will be compressed to reduce the file size. Contrast-based filters can be applied to the stitched image.

Figure 6:
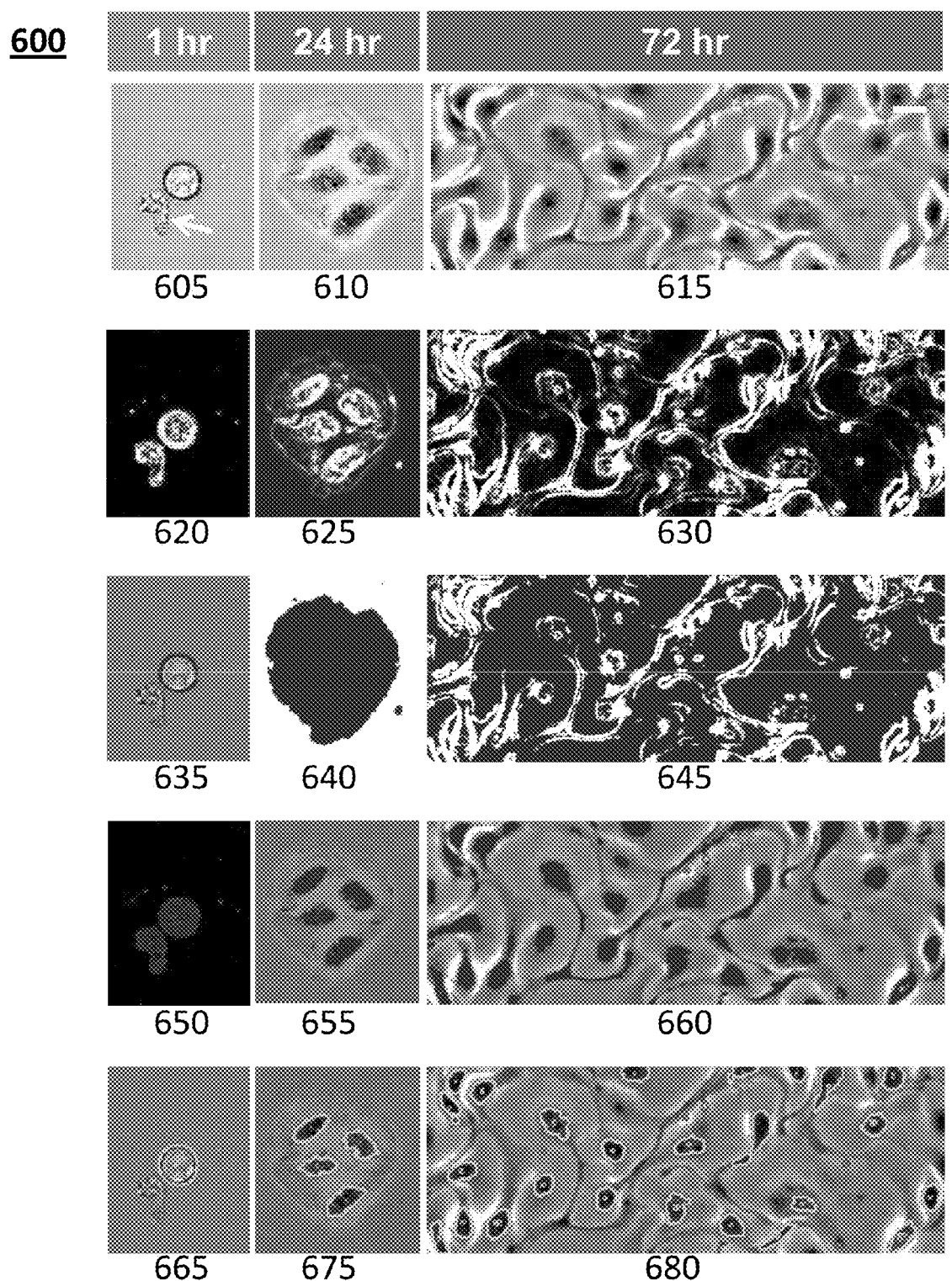
FIG. 6 depicts software analysis of live-cell images.

An example of live cell imaging and software analysis of dividing cancer cells can be seen in FIG. 6. Breast cancer cells (MDA-MB231) obtained from cell spiking experiments were imaged at one hour, 24 hours, and 72 hours 600. Raw images of breast cancer cells are shown at one hour 605; 24 hours 610; and 72 hours 615. The white arrow in panel 605 points to a white blood cell that is attached to the substrate; the circular cell in panel 605 is a breast cancer cell attached to the substrate. In panels 620, 625, and 630 the same images are depicted but the images have been binned and a variance filter has been applied. In panels 635, 640, and 645, images have been automatically thresholded and segmented to provide the total surface area of a given cell colony (black and white image adapted from an original color image). Next, panels 650, 655, and 660 depict threshold-segmentation of the cell nuclei (adopted from a color image). Finally, cell nuclei are enumerated in panels 665, 675 and 680 (adopted from a color image).

The software program can determine the number of total cells, number of viable and non-viable cells, and the number of actively dividing cells and the number of cell colonies. The ratios between viable and non-viable cells, and the ratio between dividing and non-dividing cells are can be used to determine the aggressiveness or malignant potential of a patient's CTCs. Rapidly dividing cells are considered an 'aggressive' class of CTCs.

iii. Identification and Classification Parameters

The software can use the following parameters to identify and classify target cell subpopulations: cell size, cell shape, cell movement, nucleus size and cell division rate. The software can integrate the parameters. The software can process the parameters in cycles, processed either sequentially or tangentially using multicore computer chips. Optionally, a user may assign different weights to each of the said parameters.

The software package has been developed using ImageJ (Collins (2007) ImageJ for microscopy. *BioTechniques* 43:S25-S30, incorporated herein by reference) to create new plugins for the detection and measurement of cell proliferation. A push-button JAVA-based plugin for ImageJ automatically detect and measure cell number and cell division rates for a given image series. A graphical user interface-based plugin can support user inputs and batch processing capabilities. The software can consist of four distinct scripts (or processes) that are run sequentially to produce a total cell count.

The software program can be used to identify proliferating cells by integrating one or any combination of the following five parameters: (1) overall cell size; (2) cell shape; (3) cell movement; (4) cell nucleus size; (5) cell division rate; or any combination thereof. The software identification process is capable of cycling through the aforementioned five parameters. The parameters can be processed sequentially or tangentially through the use of multi-core computer chips. The cell division rate parameter is used to subclassify cells (e.g., to classify CTCs as being of a certain metastatic potential). The software allows each of the five parameters to be weighted differently by the user.

The software program can be used to identify percentage of viable cells of a given population by determining the exact location or position at each acquisition time point. The software can measure the shape and movement of a single cell. Cell shape, deformability, and movement parameters may be used to determine if cells are viable. Conversely, cells that do not undergo morphological changes or exhibit movement are considered non-viable.

The software program can measure cell division rates by calculating the overall surface area of a given cell or cell colony for each stitched image at given time point. A single proliferating cell exhibiting a surface area change of at least four times its original surface area during the entire image acquisition step can be considered actively dividing. Cells or cell colonies exhibiting an increase in size can be further analyzed by enumerating the nuclei of said cells to determine their exact number.

iv. Enhancement of Cell Detection

In some embodiments, the visualization of target cell subpopulations can be enhanced by using cell permeable dyes and/or antibodies against cell-adhesion proteins. Cell-permeable fluorescent dyes may be used to aid the analysis software to determine the overall cell and nuclei shape, size, and number. There are several cell-permeable dyes known to those skilled in the art. Some non-limiting examples include: calcium-based dyes (e.g., Calcium-Green-1 AM; Life Technologies) or fluorescently conjugated dextran.

Analysis software may also be aided through the visualization of mitochondria. Mitochondria specific antibodies or permeable dyes (e.g., MitoTracker; Life Technologies) may be used to enhance the detection of target cell subpopulations. Furthermore, the complete absence or overabundance of mitochondria for given cell subpopulation or colony can be used as an additional parameter for subclassification, however those skilled in the art will recognize there may be other cell-permeable fluorescent dyes that may be used to aid detection.

Antibodies directed against cell surface molecules, such as cell adhesion molecules may also be used to enhance detection of a target cell subpopulation. Analysis software can be aided through the use of known biomarkers that mark a target cell subpopulation. Targeting antibodies that are conjugated to a detection moiety can be used to enhance detection, and subclassify cells based on the presence of specific biomarkers. Known biomarkers for CTCs include EpCAM, EGFR, and CD 133, however those skilled in the art will recognizes there have been other biomarkers identified.

Figure 9:
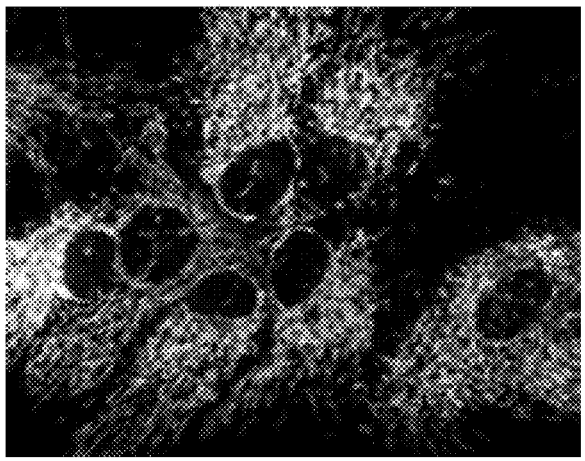
FIG. 9 illustrates how target cell subpopulations can be labeled to enhance detection using a mitochondrial marker or a fluorescently labeled antibody directed against a cell-adhesion molecule.
Figure 9:
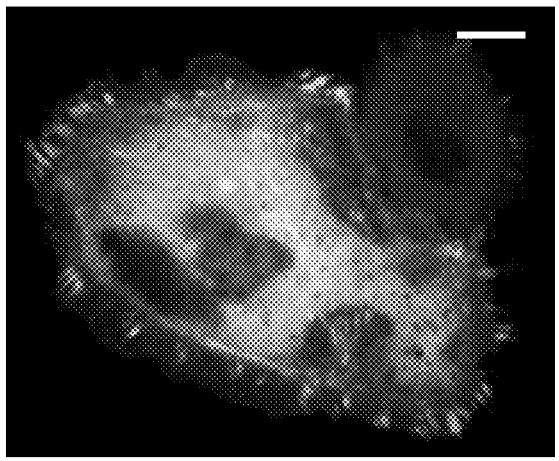

FIG. 9 is one such example of enhanced cell detection (figure adopted from a color image). Panel 905 shows labeled cancer cells; the mitochondria of the cells are labeled with MitoTracker. Panel 910 shows a cancer cell labeled with fluorescently conjugated antibodies against the cell adhesion protein, paxillin.

B. System for Software Facilitation

Figure 11:
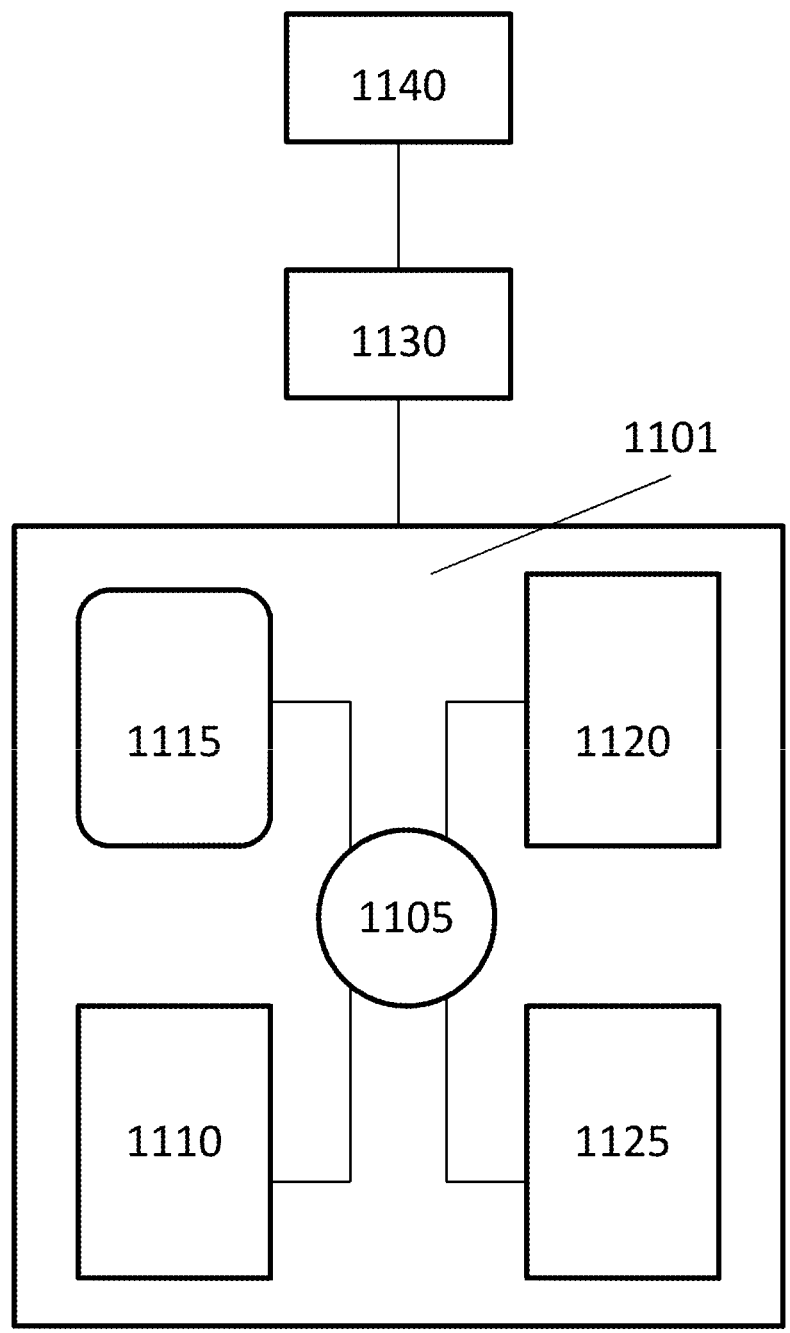
FIG. 11 depicts a system for software facilitation.
Figure 12:
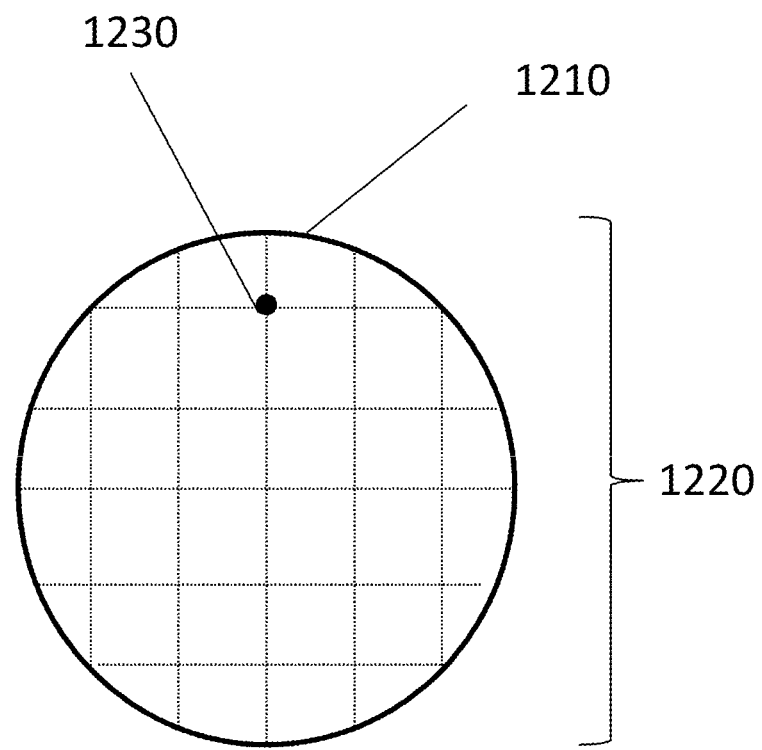
FIG. 12 depicts a virtual grid coordinate system created by the analysis software.

Another aspect of the invention provides a system that is configured to implement the methods of the disclosure. The system can include a computer server ("server") that is programmed to implement the methods described herein. FIG. 11 depicts a system 1100 adapted to enable a user to detect, analyze, and process images of cells. The system 1100 includes a central computer server 1101 that is programmed to implement exemplary methods described herein. The server 1101 includes a central processing unit (CPU, also "processor") 1105 which can be a single core processor, a multi core processor, or plurality of processors for parallel processing. The server 1101 also includes memory 1110 (e.g. random access memory, read-only memory, flash memory); electronic storage unit 1115 (e.g. hard disk); communications interface 1120 (e.g. network adaptor) for communicating with one or more other systems; and peripheral devices 1125 which may include cache, other memory, data storage, and/or electronic display adaptors. The memory 1110, storage unit 1115, interface 1120, and peripheral devices 1125 are in communication with the processor 1105 through a communications bus (solid lines), such as a motherboard. The storage unit 1115 can be a data storage unit for storing data. The server 1101 is operatively coupled to a computer network ("network") 1130 with the aid of the communications interface 1120. The network 1130 can be the Internet, an intranet and/or an extranet, an intranet and/or extranet that is in communication with the Internet, a telecommunication or data network. The network 1130 in some cases, with the aid of the server 1101, can implement a peer-to-peer network, which may enable devices coupled to the server 1101 to behave as a client or a server. The microscope and micromanipulator can be peripheral devices 1125 or remote computer systems 1140.

The storage unit 1115 can store files, such as individual images, time lapse images, data about individual cells, cell colonies, or any aspect of data associated with the invention. The data storage unit 1115 may be coupled with data relating to locations of cells in a virtual grid.

The server can communicate with one or more remote computer systems through the network 1130. The one or more remote computer systems may be, for example, personal computers, laptops, tablets, telephones, Smart phones, or personal digital assistants.

In some situations the system 1100 includes a single server 1101. In other situations, the system includes multiple servers in communication with one another through an intranet, extranet and/or the Internet.

The server 1101 can be adapted to store cell profile information, such as, for example, cell size, morphology, shape, migratory ability, proliferative capacity, kinetic properties, and/or other information of potential relevance. Such information can be stored on the storage unit 1115 or the server 1101 and such data can be transmitted through a network.

Methods as described herein can be implemented by way of machine (or computer processor) executable code (or software) stored on an electronic storage location of the server 1101, such as, for example, on the memory 1110, or electronic storage unit 1115. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110. Alternatively, the code can be executed on a second computer system 1140.

Aspects of the systems and methods provided herein, such as the server 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tantible "storage" media, terms such as computer or machine "readable medium" refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

The results of cell monitoring can be presented to a user with the aid of a user interface, such as a graphical user interface.

VII. SYSTEM HARDWARE

A. Microscope

Microscopy hardware control is developed on top of the open-source, java-based image acquisition software, μManager (Arthur Edelstein, et al. (2010), Computer Control of Microscopes Using μManager. Current Protocols in Molecular Biology 14.20.1-14.20.17, incorporated herein by reference). Custom drivers and scripts are used to control the following microscopy-essential peripherals: image acquisition camera, camera-shutter, motorized linear-encoded X-Y stage, piezo-driven Z-axis stepper, and near-infrared based autofocus.

To view cells, an inverted microscope with a customized environmental chamber can be used. The customized environmental chamber may regulate temperature, $CO_2$, and oxygen levels with 0.1% precision. The microscope can include 5×, 10×, 20×, 40× non-oil objectives with fluorescence capabilities but other objectives are contemplated. The inverted microscope may include a motorized stage and hardware-based auto-focusing with a brightfield light source, with phase-shifted polarization filters to enhance contrast for the detection of cells. The light source, can be halogen, xenon, mercury, solid-state lasers or light-emitting diode.

B. Micromanipulation

Cells can be collected or marked using micromanipulation. Micromanipulation can be accomplished using any techniques known in the art, including a motorized micromanipulator and transjector or laser microdissection. The user can revisit the location of specific colonies or cells of particular interest. This can allow, for example, the user to individually grab cells for targeted biomedical studies at the single cell level, harvest cells for further culturing experiments, or perform chemosensitivity testing.

Figure 8:
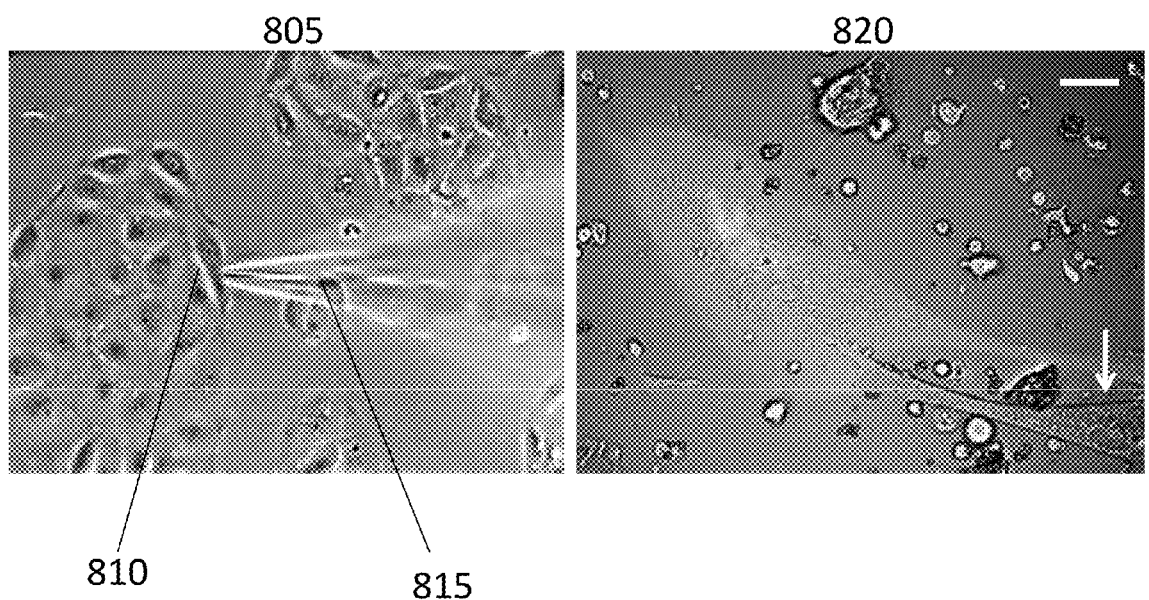
FIG. 8 depicts a motor-driven micromanipulator selecting and injecting single cells.

A motorized micromanipulator and transjectior is shown in FIG. 8. Panel 805 depicts a single cell selection; the injection/selection needle of a motor-driven micromanipulator 815, isolates a single cancer cell 810 from a colony of cells. Panel 820 depicts the injection of a single cell with fluorescently conjugated dextran; the white arrow points to an uninjected cancer cell (image adopted from color image).

C. Automated Cell Culture System

Figure 14:
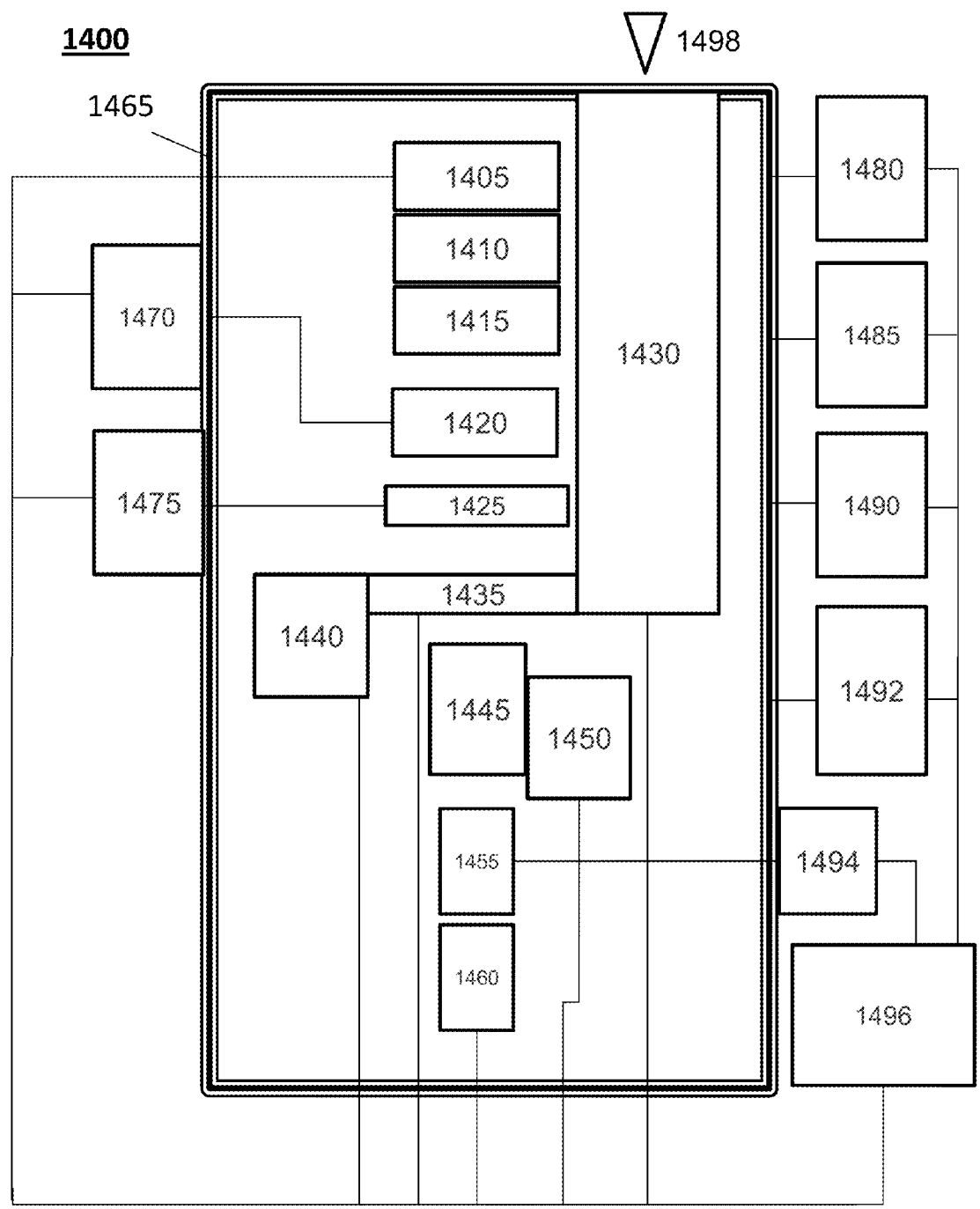
FIG. 14 depicts an automated cell culture system design.

Methods described herein can be implemented by a cell culture system. FIG. 14 depicts a system 1400 to automate cell culture. The system 1400 includes a light source 1405 which can be bright field and can provide illumination for phase-based light microscopy. The light source 1405 can be filament or light emitting diode (LED) based. The system 1400 can also include a phase contrast ring with a turret 1410. In some instances, the turret can be motorized and compatible contrast rings can be paired to the proper objective 1445.

The system 1400 may optionally include a light condenser 1415. In some instances, a light condenser 1415 may be used to focus the light source which in some instances can improve the contrast of cells. The system may also optionally include a cell selector (i.e. a cell picker) 1420. In some instances the cell selector can select single cells (e.g. a micromanipulator-based cell selection needle or a laser-aided microdissection tool).

The system 1400 may optionally have a liquid dispenser 1425. The liquid dispenser 1425 can be used as a mechanism to handle the delivery and transport of media. The liquid dispenser can be syringe-based. The liquid dispenser 1425 can be have one or multiple dispensing ports (e.g. 1, 2, 6, 12, 24, 96 etc.) to dispense liquid into multi-well plates (e.g. 1-well, 2-well, 6-well, 12-well, 24-well, 96-well plates, etc.). In some instances, the liquid dispenser can be a modular add-on with automated liquid dispensing capabilities (e.g. Eppendorf's epMotion, GE's IN CELL Analyzer 6000).

The system 1400 may optionally have a plate loader 1430. The plate loader 1430 may comprise a motorized plate container that can have a capacity to hold a minimum of 1, 2, 3, 4, 5, 6, 10, 15, 20, 25, or 30 plates. The plate loader can have a modular design to allow for additional plate capacity. In some instances, the plate loader can robotically handle plates for example, to place a plate on the X-Y stage of a microscope for imaging (e.g. ASI's robot plate loader).

The system 1400 may have an X-Y-Stage 1435. The X-Y-Stage 1435 may include a linear encoder for precise movement. The X-Y-Stage 1435 can be comprised of a stage that can hold a single plate (e.g. ASI MS-2000 Flat Top XYZ Automated Stage). The X-Y-Stage 1435 can be comprised of a large format stage with capacity to hold one, two, three, four, five, six or more plates simultaneously.

The system 1400 can have a Z-Stepper 1440. The Z-stepper can be a motorized, piezo-driven, Z-axis control that can, e.g., be used for multiple-plane imaging.

The system 1400 can have one or more objectives. The objectives can be approximately 1×, 5×, 10×, 15× 20×, 30×, 40×, 60×, and/or 100×. In some instances, the objectives 1445 will be attached to a motorized objective turret. The objectives 1445 can be phase objectives. The objectives 1445 can be microscope objectives that are suitable for both brightfield and fluorescence imaging (e.g. Ziess Plan-Neofluar objectives). In some embodiments, the objectives 1445 must be compatible with a hardware-based auto-focus system (e.g. Nikon's Perfect Focus System).

The system 1400 can optionally contain an auto-focus system 1450. The auto-focus system 1450 can use hardware-based image auto-focusing (e.g. Nikon's Perfect Focus System).

The system 1400 can optionally contain a filter 1455. The filter 1455 can be an illumination filter. The filter 1455 can be dichroic. Dichroic mirrors can be used in conjunction with appropriate excitation and emission filters to fluorescence imaging—compatible wavelengths can be, for example, approximately 360 nm, 488 nm, and 568 nm.

The system 1400 can have a camera 1460. The camera 1460 may be charge coupled device (CCD) or complementary metal oxide semiconductor (CMOS). The camera 1460 can be compatible with fluorescence, brightfield or both. The camera 1460 can be liquid cooled. The camera 1460 can be wide-field-of-view. The camera 1460 can have wide angle imaging sensors. The camera 1460 can also comprise back-side illumination based image sensors. The camera 1460 can have the capability to transmit information. The capability to transmit information can be known fast-transfer method (e.g. firewire or USB 3.0 ports).

The system 1400 can contain an environmental chamber 1465. The environmental chamber 1465 can comprise a sealed and light-controlled (e.g. dark) environment. The environmental chamber 1465 may optionally use an air-lock system. In some instances the use of an air-lock system can be used when access to one or more plates is needed while experiments are in progress. The environmental chamber 1400 can also comprise an ability to support a pressurized environment. In some instances, the pressurized environment can be approximately 1, 2, 3, 4, 5, 6, 7, 8, 9, 10, 11, 12, 13, 14, 15, PSI over atmospheric pressure. In some embodiments, the environmental chamber 1465 will be constructed to support sterilization or cleaning protocols. In some embodiments, the environmental chamber may comprise a de-humidificaiton, heating, vacuum pressure control and/or any combination thereof.

The system 1400 may optionally have a manipulator 1470. The manipulator 1470 may be used to control the cell selector 1420. The manipulator 1470 may be controlled by a user (e.g. joy-stick) or may be controlled by software. The manipulator may be a mechanical and pressure-hub for handling of single cells. (e.g. Eppendorf's transjector, manipulator, Cell TRAM VARIO).

The system 1400 may optionally have a liquid handling module 1475. The liquid handling module 1475 can be used as a reservoir for liquids (e.g. media, waste media). The liquid handling module 1475 can be used to support one or more liquids. The liquid handling module 1475 can in some instances support 1, 2, 3, 4, 5, 6, 7, 8, 9 10, 11, 12, 13, 14, 15, 16, 17, 18, 19, and/or 20 solutions. In some embodiments, the liquid handling module 1475 can comprise automated sterilization capabilities.

The system 1400 can have a humidification regulator 1480. The humidification regulator 1480 can be used to dehumidify. In some instances, dehumidification may enhance imaging and may increase the life of internal electronics.

The system 1400 can have a heating element 1485. The heating element 1485 may be used to warm the contents of the environmental chamber 1465. In some embodiments, the contents of the environmental chamber may be heated to approximately 26, 27, 28, 29, 30, 31, 32, 33, 34, 35, 36, 37, 38, 39, 40, 41, 42, 43, 44, or 45 degrees Celsius. In some embodiments, the heating element 1485 will comprise an integrated temperature system that can control the temperature with automated feedback.

The system 1400 can have a gas inlet 1490. The gas inlet 1490 can have integrated gas controls and support for individual gas lines (i.e. dual valve support). In some instances the gas inlet 1490 can control the level of atmospheric gases, such as nitrogen, carbon dioxide, and/or oxygen.

The system 1400 can have a pressurized vacuum pump 1492. The pressurized vacuum pump 1492 can have a pressure gauge and/or an integrated pressure sensor or manifold. The pressurized vacuum pump 1492 can have the capability to supply a pressure of approximately 1, 2, 3, 4, 5, 6, 7, 8, 9, or 10 PSI over atmospheric pressure. In some embodiments, the pressurized vacuum pump 1492 is capable of supplying pressure to an estimated approximate volume of 10 to 18 cubic feet.

The system 1400 can optionally have a fluorescent light source 1494. The fluorescent light source 1494 can be xenon. The fluorescent light source 1494 can be from a mercury-based lamp. The fluorescent light source 1494 can be from a solid state, or laser-diode based illumination source.

The system 1400 can have a system for data storage 1496. The system for data storage 1495 can comprise any number of storage type media can include any or all of the tangible memory of the computers, processors or the like, or associated modules thereof, such as various semiconductor memories, tape drives, disk drives and the like, which may provide non-transitory storage at any time for the software programming. The system for data storage can also comprise any number of data communication types e.g. through the Internet or various other telecommunication networks. Data may be transmitted through optical, electrical, and/or electromagnetic waves, such as used across physical interfaces between local devices, through wired and optical landline networks and over various air-links. The physical elements that carry such waves, such as wired or wireless likes, optical links, or the like, also may be part of the system for data storage. As used herein, unless restricted to non-transitory, tangible data storage media, terms such as computer or machine "readable medium" refer to any medium that participates in providing instructions to a processor for execution. Hence data storage, may take many forms, including but not limited to, tangible storage medium, a carrier wave medium, or physical transmission medium. Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying data for storage. In some embodiments, the system for data storage can be a multi-core processor.

The system 1400 can have an instrument access door 1498. The instrument access door 1498 may provide a port of entry to the plate loader 1430 and/or the environmental chamber 1465. The instrument access door 1498 may integrate an air-lock system.

The system 1400 can provide a platform for high-throughput uses of the invention as described herein.

VIII. APPLICATIONS

A. Source of Valuable Cells

There are several practical applications of the present invention. The ability to enrich rare target subpopulations of cells has value as a commodity to be used for basic research, medical treatments, medical research, development and discovery of drugs and biologics, high throughput screens, antibody development, and vaccine development. CTCs, CSCs, HSCs, and EPCs are examples of cells that circulate in the blood but have been difficult to isolate and enrich in quantities sufficient for practical laboratory or medical purposes. In another application of this invention, cultured target cell subpopulations with varying functional traits can provide a platform for highly targeted biomarker discovery. Genomic, proteomic, and metabolic analysis can be conducted on these cultured cells and the ability to generate a commercially available source of these rare cells is important for the identification of novel biomarkers to be used for development of cancer therapies (e.g. drug development), cancer vaccines, cancer screening and diagnostics, personalized antibody development, hematopoietic stem cell transplantation, organ transplantation, and cardiovascular disease treatment.

B. Personalized Medicine

Figure 10:
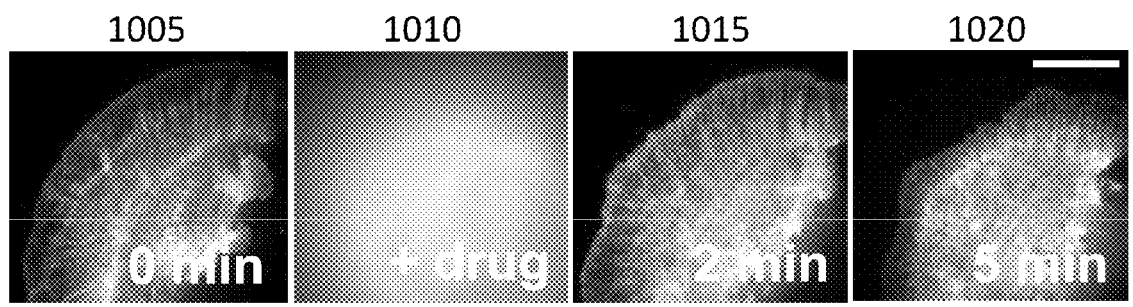
FIG. 10 depicts a chemosensitivity assay conducted on single cells.

Target cell subpopulations can be used for personalized medicine. In the instance of CTCs and CSCs, cells can be used for chemosensitivity testing on whereby standard and exploratory chemotherapy regimens can be tested on cultured CTCs and determination of the effects of chemotherapy drugs on CTCs, including cell viability and cell division rates measurement to determine the efficacy of a given drug. An example of how a chemosensitivity assay can be applied is depicted in FIG. 10. A chemosensitivity assay on single cells shows loss of adhesions and retraction of the plasma membrane 1000. In this example, Rho Kinase inhibitor, Y-27632 was used (Ishizaki et al. 2000 Pharmacological Properties of Y-27632, a specific inhibitor of rho-associated kinases. Mol Pharmacol. 57(5):976-83). Panel 1005 shows a single cell before Y-27632 treatment. Panel 1010 shows an image of the cell upon addition of Y-27632. The plasma membrane of the cell retracts upon drug treatment after 2 minutes 1015 and 5 minutes 1020.

Another application of the present invention is to monitor patient response to a given cancer therapy conducted by serial monitoring of their CTC population as they undergo treatment. Blood samples can be analyzed on a regular basis, before, during and after treatment whereby a positive response to therapy would results in decreased CTC viability and lower division rates.

Another application of this invention is to monitor patients who are currently in remission to investigate the potential of cancer relapse. Serially testing of their blood for CTCs can be conducted on a regular basis, to determine the potential or likelihood for cancer relapse. In some cases, serial testing can result in earlier detection of relapse.

Another application of the disclosure is for high throughput drug discovery and as a direct research platform for basic research. A large supply of cells is needed to conduct a meaningful study on the efficacy of a drug on a particular cell type. Additionally, comparing the effectiveness of different drug treatments on different types of cells requires a large amount of cells. The disclosure provides for a research platform for basic research allowing for scientists to automate or partially automate the process of isolating cell types; thereby allowing for high throughput experiments to be possible.

B. Treating a Patient

The invention described herein provides data that can be used for a medical professional to treat a patient. In a preferred embodiment, the classification of cells can direct treatment of a patient. Treatment of a patient can include diagnosis, prognosis or theranosis. Diagnoses can comprise determining the condition of a patient. Diagnosis can be conducted at one time point or on an ongoing basis. For example, a patient can be diagnosed with cancer. In another example a cancer patient who is in remission could be routinely screened to determine if a cancer relapse has occurred. Prognosis can comprise determining the outcome of a patient's disease, the chance of recovery, or how the disease will progress. For example, identifying CTCs of a certain type can provide information upon which a prognosis may be based. Theranosis can comprise determining a therapy treatment. For example, a patient's cancer therapy treatment can be comprised of chemotherapy, radiation, drug treatment, no treatment or any combination thereof. A patient may be monitored, for example by serial blood testing, to measure CTC populations before, during and after a patient undergoes treatment. A positive response to therapy would result in a decreased CTC viability and lower division rates.

In the case of isolated and classified CTCs from a cancer patient, the presence or absence of CTCs may aid or form the diagnosis of cancer. Prognosis of disease may be aided by the types of CTCs present in the patient's blood. Theranosis can be aided based on knowledge of the type of CTCs present. Theranosis may also be aided by using isolated CTCs to test the probability of success of various treatments, such as chemotherapeutic agents most likely to successful.

IX. CONCLUSION

The inventions herein provide a new approach for the detection and enrichment of target cell subpopulations from a heterogeneous cell population. The method can be applied whenever one has a heterogeneous cell population and enrichment of a target cell subpopulation is needed.

The above description is illustrative and not restrictive. Many variations of the invention will become apparent to those of skill in the art upon review of this disclosure. Merely by way of example, while the invention is illustrated primarily with regard to enrichment of target cell subpopulations, including CTCs, CSCs, HSCs, and EPCs from bodily fluids, the invention is not so limited. The scope of the invention should, therefore, be determined not with reference to the above description but should be determined with reference to the claims along with their full scope of equivalents.

What is claimed is:

1. A method for isolating a target cell subpopulation of circulating tumor cells (CTCs) from a plurality of cells, the method comprising:
    a) incubating the plurality of cells under both a positive pressure of about 2 PSI over atmospheric pressure and a hypoxic condition of about 2% $O_2$ in an enclosed environment chamber, wherein the enclosed environment chamber is configured to produce the positive pressure and hypoxic condition;
    b) performing an assay to determine size, morphology, a physical property, a biological property, or a kinetic property of the target cell subpopulation of CTCs;
    c) isolating the target cell subpopulation of CTCs based on the size, morphology, a physical property, a biological property, or a kinetic property of the target cell subpopulation of CTCs based on the results of the assay; and
    d) growing the isolated target cell subpopulation of CTCs under both the positive pressure of about 2 PSI over atmospheric pressure and the hypoxic condition of about 2% $O_2$ to form a large supply of cells, which can then be used for a research purpose.

2. The method of claim 1, wherein one or more cells from the plurality of cells are cultured.

3. The method of claim 2 wherein the one or more individual cells are isolated using micromanipulation.

4. The method of claim 1, wherein the plurality of cells are derived from a bodily fluid sample.

5. The method of claim 1, wherein the plurality of cells comprises:
    a) a bodily fluid; and
    b) cells from a different source that have an ability to be marked.

6. The method of claim 1, the method further comprising incubating of the plurality of cells in an enrichment medium.

7. The method of claim 6, where the enrichment media is selected from the group consisting of Plating Culture Medium; Type R Long Term Growth Medium; Type DF Long Term Growth Medium; Type D Long Term Growth Medium; MEF—Enrichment Medium; and any combination thereof.

8. The method of claim 1, the method further comprising contacting the plurality of cells with a substrate.

9. The method of claim 8, wherein the substrate is selected from the group consisting of GOL Substrate, GEL Substrate, and a cell monolayer.

10. The method of claim 8, wherein the substrate comprises a configuration is selected from the group consisting of single layer, two layer, middle layer(s), and inverted configuration.

11. The method of claim 1, further comprising a computer readable medium comprising code that, upon execution by one or more processors, controls the pressure or oxygen level.

12. The method of claim 1, further comprising incubating the plurality of cells under an increased level of CO2 as compared to atmospheric CO2 levels.

13. The method of claim 1, further comprising incubating the plurality of cells in a humidity chamber.

14. The method of claim 1, wherein the assay comprises imaging at least one cell from the target cell subpopulation of CTCs.

15. The method of claim 1, wherein the assay comprises measuring a cell division rate of the target cell subpopulation of CTCs.

16. The method of claim 1, wherein the assay comprises detection of the target cell subpopulation of CTCs using a cell permeable dye.

17. The method of claim 1, wherein the assay comprises detection of the target cell subpopulation of CTCs using an antibody.

18. The method of claim 17, wherein the antibody targets a cell surface protein in the target cell subpopulation of CTCs.

19. The method of claim 1, wherein performing the assay further comprises genomic analysis of the target cell subpopulation of CTCs.

20. The method of claim 1, wherein performing the assay further comprises proteomic analysis of the target cell subpopulation of CTCs.

21. The method of claim 1, wherein performing the assay further comprises measuring biomarker expression in the target cell subpopulation of CTCs.

22. The method of claim 1, wherein the research purpose comprises any of discovery and development of drugs, high throughput screening, antibody development, vaccine development, and biomarker discovery.

23. The method of claim 22, wherein the research purpose comprises any of genomic, proteomic, and metabolic analysis.

24. The method of claim 22, wherein the research purpose comprises development of theranostic assays.

25. The method of claim 22, wherein the research purpose comprises the development of cells for transplantation therapies, the transplantation therapies comprising any of any of hematopoietic stem cell transplantation, organ transplantation, and cardiovascular cell transplantation.

* * * * *